(12) United States Patent
Helmer

(10) Patent No.: US 12,718,711 B2
(45) Date of Patent: Aug. 25, 2026

(54) ELECTRONIC LABEL FOR A DRUG DELIVERY DEVICE

(71) Applicant: Sanofi, Paris (FR)

(72) Inventor: Michael Helmer, Frankfurt am Main (DE)

(73) Assignee: SANOFI, Paris (FR)

( * ) Notice: Subject to any disclaimer, the term of this patent is extended or adjusted under 35 U.S.C. 154(b) by 209 days.

(21) Appl. No.: 17/769,106

(22) PCT Filed: Oct. 26, 2020

(86) PCT No.: PCT/EP2020/080028
§ 371 (c)(1),
(2) Date: Apr. 14, 2022

(87) PCT Pub. No.: WO2021/083834
PCT Pub. Date: May 6, 2021

(65) Prior Publication Data

US 2023/0108921 A1 Apr. 6, 2023

(30) Foreign Application Priority Data

Oct. 28, 2019 (EP) .................................... 19306394

(51) Int. Cl.
*G09F 3/20* (2006.01)
*A61M 5/31* (2006.01)
(Continued)

(52) U.S. Cl.
CPC ......... *G09F 3/208* (2013.01); *A61M 5/31566* (2013.01); *A61M 2005/3126* (2013.01);
(Continued)

(58) Field of Classification Search
CPC ............ G09F 2003/0272; G09F 3/208; A61M 2205/52; A61M 2205/502; A61M 2005/3126; A61M 5/31566
See application file for complete search history.

(56) References Cited

U.S. PATENT DOCUMENTS 2,828,473 A 3/1958 High
2,828,743 A 4/1958 Ashkenaz et al.
(Continued)

FOREIGN PATENT DOCUMENTS

CN 102481230 A 5/2012
CN 104470562 A 3/2015
(Continued)

OTHER PUBLICATIONS

International Preliminary Report on Patentability in International Appln. No. PCT/EP2020/080028, dated May 12, 2022, 8 pages.
(Continued)

*Primary Examiner* — David R Dunn
(74) *Attorney, Agent, or Firm* — Bond, Schoeneck & King, PLLC

(57) ABSTRACT

The present disclosure relates to an electronic label for a drug delivery device configured for administering a medicament to a patient. The electronic label includes a flexible substrate configured for attachment to a body. The electronic label further includes an electronic display located on the flexible substrate, wherein the electronic display is configured to display a first information content of a first information type, a second information content of a second information type, and a third information content of the first or of the second information type. The electronic label includes a processor connected to the electronic display, which is configured to modify or to control a visual appearance of the electronic display by visualizing at least a portion of the first information content and at least a portion of the
(Continued)

third information content separately, simultaneously, sequentially or alternately on the electronic display.

17 Claims, 9 Drawing Sheets

(51) Int. Cl.
*A61M 5/315* (2006.01)
*G09F 3/02* (2006.01)

(52) U.S. Cl.
CPC ... *A61M 2205/502* (2013.01); *A61M 2205/52* (2013.01); *G09F 2003/0272* (2013.01)

(56) References Cited

U.S. PATENT DOCUMENTS 2,880,723 A 4/1959 Adams
3,158,155 A 11/1964 Simon et al.
3,375,825 A 4/1968 Keller
3,557,787 A 1/1971 Cohen
3,736,932 A 6/1973 Satchell
3,820,652 A 6/1974 Thackston
4,045,954 A * 9/1977 Ganter .................. G04C 21/02 968/581
4,181,223 A 1/1980 Millet
4,303,069 A 12/1981 Cohen
5,458,580 A 10/1995 Hajishoreh
5,658,259 A 8/1997 Pearson et al.
5,902,277 A 5/1999 Jentzen
5,928,205 A 7/1999 Marshall
6,810,290 B2 * 10/2004 Lebel ....................... G06F 8/65 607/60
8,514,086 B2 * 8/2013 Harper .................. A61B 5/145 340/505
9,254,366 B2 2/2016 Matthias
9,782,543 B2 * 10/2017 Groeschke ........ A61M 5/31568
10,179,207 B2 * 1/2019 Haupt ..................... A61M 5/24
10,183,119 B2 * 1/2019 Andersen ............ A61M 5/2455
10,207,058 B2 * 2/2019 Riedel .................... B42D 25/20
10,610,645 B2 4/2020 Helmer
2002/0186214 A1 * 12/2002 Siwinski ............. H04W 52/027 345/212
2003/0144633 A1 7/2003 Kirchhofer
2004/0034323 A1 2/2004 Manthey
2004/0039337 A1 2/2004 Letzing
2004/0110326 A1 * 6/2004 Forbes ................ H01L 27/1262 257/E21.414
2006/0176278 A1 * 8/2006 Mathews ................. G09G 3/20 345/168
2009/0069745 A1 * 3/2009 Estes ................. A61M 5/16804 604/67
2009/0245280 A1 * 10/2009 Rajamani .......... H04W 52/0235 370/468
2011/0224640 A1 9/2011 Kuhn et al.
2011/0276008 A1 11/2011 Matthias
2012/0179109 A1 7/2012 Takemoto et al.
2012/0279996 A1 11/2012 Pappalardo et al.
2014/0058749 A1 * 2/2014 Galley .................. G16H 40/63 705/3
2015/0119815 A1 4/2015 Fuke et al.
2015/0246179 A1 * 9/2015 Zur ....................... G16H 40/67 604/207
2016/0082192 A1 * 3/2016 Veasey ................ A61M 5/3155 604/211
2017/0232203 A1 * 8/2017 Krusell .................. A61M 5/24 604/207
2017/0290987 A1 10/2017 Mandaroux et al.
2018/0028747 A1 2/2018 Hanson et al.
2018/0042559 A1 * 2/2018 Cabrera, Jr. ........ G06F 3/04847
2018/0307320 A1 * 10/2018 Ananthapur Bache ..................... G06F 3/04845
2018/0353700 A1 * 12/2018 Säll .................. A61M 5/31568
2019/0009032 A1 * 1/2019 Hautaviita .......... A61M 5/3157
2019/0184094 A1 * 6/2019 Sjolund ................ A61B 5/7405
2019/0308007 A1 10/2019 Mudd et al.

FOREIGN PATENT DOCUMENTS

EP 2875838 A1 5/2015
EP 3068468 4/2018
JP S51000398 B 1/1976
JP H09066106 A 3/1997
JP H11502448 A 3/1999
WO 9630065 A1 10/1996
WO WO 2004/078239 9/2004
WO WO 2004/078240 9/2004
WO WO 2004/078241 9/2004
WO 2010139671 A1 12/2010
WO 2012063065 A1 5/2012
WO 2014013594 A1 1/2014
WO WO 2015/071354 5/2015
WO WO 2018/185317 10/2018
WO WO 2018/206442 11/2018

OTHER PUBLICATIONS

International Search Report and Written Opinion in International Appln. No. PCT/EP2020/080028, dated Dec. 15, 2020, 10 pages.

PCT International Preliminary Report on Patentability in International Application No. PCT/ EP2016/078261, dated May 29, 2018, pp. 1-6.

PCT Internatoinal Search Report and Written Opinion in International Application No. PCT/ EP2016/078261, dated Feb. 23, 2017, pp. 1-8.

* cited by examiner 114
116
drug name
411
451
118
110
remove cap
452
128
114
$t_0$ drug name
411
110
set dose of size X
453
$t_1$ drug name
411
110
inject dose
454
$t_2$ drug name
411
110
injection completed
458
wait xx seconds
459
$t_3$

ELECTRONIC LABEL FOR A DRUG DELIVERY DEVICE

CROSS REFERENCE TO RELATED APPLICATIONS

The present application is the national stage entry of International Patent Application No. PCT/EP2020/080028, filed on Oct. 26, 2020, and claims priority to Application No. EP 19306394.8, filed on Oct. 28, 2019, the disclosures of which are incorporated herein by reference.

TECHNICAL FIELD

The present disclosure relates to the field of electronic labels, in particular to electronic labels for drug delivery device, such as injection devices. Moreover, the present disclosure relates to a multifunctional label that is configured to change its visual appearance, either autonomously or in response to an interaction with a user. In another aspect the disclosure relates to a drug delivery device equipped with an electronic label. In still another aspect the disclosure relates to a method of visualizing numerous information contents of different information type on an electronic label for use with a drug delivery device

BACKGROUND

Drug delivery devices for setting and dispensing a single or multiple doses of a liquid medicament are as such well-known in the art. Generally, such devices have substantially a similar purpose as that of an ordinary syringe.

Drug delivery devices, such as pen-type injectors have to meet a number of user-specific requirements. For instance, with patient's suffering chronic diseases, such as diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Such injection devices should provide setting and subsequent dispensing of a dose of a medicament of variable size. Moreover, a dose setting as well as a dose dispensing procedure should be easy to operate and has to be unambiguous.

SUMMARY

Drug delivery devices include a housing or a particular cartridge holder, adapted to receive a cartridge at least partially filled with the medicament to be dispensed. The device further includes a drive mechanism, usually having a displaceable piston rod to operably engage with a bung or piston of the cartridge. By means of the drive mechanism and its piston rod, the bung or piston of the cartridge is displaceable in a distal or dispensing direction and may therefore expel a predefined amount of the medicament via a piercing assembly, e.g. in form of an injection needle, which is to be releasably coupled with a distal end section of the housing of the drug delivery device.

The medicament to be dispensed by the drug delivery device may be provided and contained in a multi-dose cartridge. Such cartridges typically include a vitreous barrel sealed in distal direction by means of a pierceable seal and being further sealed in proximal direction by the bung. With reusable drug delivery devices an empty cartridge is replaceable by a new one. In contrast to that, drug delivery devices of disposable type are to be entirely discarded when the medicament in the cartridge has been dispensed or used-up.

With some drug delivery devices, such as pen-type injection devices a user has to set a dose of equal or variable size by rotating a dose dial in a clockwise or dose-incrementing direction relative to a body or housing of the injection device. For injecting and expelling of a dose of a liquid medicament the user has to depress a trigger or dose button in a distal direction and hence towards the body or housing of the injection device. Typically, the user uses his thumb for exerting a distally directed pressure onto the dose button, which may be located at a proximal end of the dose dial and the dose dial sleeve, while holding the housing of the injection device with the remaining fingers of the same hand.

For mechanically implemented injection devices it is desirable to enable a precise, reliable and quasi-automated supervision and/or collection of injection-related data during use of the injection device. Moreover, there is a rising demand of user assistance for the proper and regular handling of such drug delivery or injection devices. For a successful therapy a well-defined, e.g. user specific amount of a medicament, i.e. a dose of the medicament, should be administered in accordance to a given prescription schedule, e.g. on a regular temporal basis. In some situations, a patient may have forgotten or may not be aware if a prescribed dose was recently injected or not. Moreover, the patient may not always be aware about the size of the dose to be set and injected. This is of particular relevance for patients being oblivious and/or for patients being mentally and/or physically infirm at least to a certain degree.

Generally, an electronic display offers the possibility to provide individual, appropriate as well as user-specific or device specific information to a user of a drug delivery device. Electronic displays that include a rather rigid and inflexible display structure are difficult to attach to a housing or body of a drug delivery device, especially when the drug delivery device is implemented as a portable or handheld drug delivery device, such as an injection pen.

By limiting the dimensions or size of an electronic display the legibility of an information content provided on the display may be severely affected.

It is therefore a demand, that different types of information, such as information about the medicament and/or the proper or intended handling of the drug delivery device become unequivocally and clearly visible on the outside of the injection device. Medicament-related information and/or device handling-related information should be provided in a durable and persistent way. However, with some scenarios of use some information should be provided dynamically and/or on demand, e.g. in order to assist a user in or during handling or use of the injection device.

It is therefore an aim to provide an improved display for a drug delivery device, in particular for an injection device, such as a handheld injection device. The display should provide device specific or medicament specific answers or user specific information so as to facilitate use and handling of the drug delivery device. By way of the display a rather user-friendly operation and handling of the drug delivery device should be provided. Moreover, the patient should be given the possibility to comprehensively inform himself about a proper use of the drug delivery device and about the medicament to be administered by the drug delivery device. The implementation and use of the display should be rather easy, intuitive and self-explanatory. It should be manufacturable at moderate or low costs and should be suitable for retrofitting existing drug delivery devices. The display should provide a space saving design and should conform to the geometry of a housing of an injection device.

In one aspect the disclosure relates to an electronic label for a drug delivery device, wherein the drug delivery device is configured for administering, e.g. expelling or injecting of a medicament to a patient. The drug delivery device may be implemented as an infusion device, as an injection device or as an inhaler or as a portable medical analysis device, such as a blood glucose meter. The electronic label is configured for attachment to a body of the drug delivery device. Insofar, the electronic label includes a flexible substrate that is configured for attachment to the body of the drug delivery device, typically to a body of a housing of the drug delivery device. The electronic label further includes an electronic display. The electronic display is located on the flexible substrate. Typically, also the electronic display is flexible. The electronic display is configured to display at least a first information content of a first information type, to display at least a second information content of a second information type and to display at least a third information content. The third information content is of the first information type or of the second information type.

The electronic label further includes a processor connected to the electronic display and configured to modify or to control a visual appearance of the electronic display. The processor is particularly configured to visualize or to display at least a portion of the first information content and at least a portion of the third information content separately, simultaneously, sequentially or alternately on the electronic display.

Insofar, the processor and the electronic display are configured to visualize or to display various information contents of different information type either separately, i.e. in a sequential temporal order or simultaneously, i.e. at the same time but spatially non-overlapping on the electronic display. When the portion of the first information content and the portion of the third information content are provided or illustrated separately, sequentially or alternately on the electronic display, the respective portion of the first and/or third information content may extend over the entire available display surface.

A separate and hence a sequential or alternating illustration of the portion of the first information content and the portion of the third information content allows to increase the size of characters or symbols representing the first, second or third information content to a maximum. In this way an information content, e.g. consisting of a comparatively large number of characters or words can be split or divided into numerous portions, e.g. a first portion, a second portion and a third portion of a respective first, second or third information content. The processor may be then configured to visualize or to display a temporal sequence of first, second and third portions of, e.g. a first information content separately and sequentially on the electronic display. In this way, the size of an information content to be visualized or displayed on the electronic display can be increased without any detrimental effect in terms of legibility or illustrated size of characters or symbols representing the respective information content.

Moreover, the processor and the electronic display are configured to simultaneously or to separately and sequentially visualize or display different types of information. Insofar, the electronic label is a multifunctional electronic label that is configured to provide, e.g. numerous information contents of a first information type and to provide numerous information contents of a second information type. Insofar, the electronic label is configured to provide medicament-specific information, device-specific information or user-specific information contents on the electronic display.

The processor is configured to reconfigure the visual appearance of the electronic display. With some examples, e.g. when the third information content is of the first information type the processor is configured to visualize or to display at least two different information contents of a common, e.g. of the first information type. These two information contents may be provided separately, i.e. sequentially or alternately on the electronic display. Switching between the first and the third information content may be triggered autonomously by the processor in accordance to a predefined schedule. With other examples and when the third information content is of the first information type the processor may be also configured to visualize or to display the first and the third information content simultaneously but spatially non-overlapping on the electronic display.

In situations or examples wherein the processor visualizes or displays the first and the third information content separately, sequentially or alternately, the first and third information type may be provided in spatially overlapping regions of the electronic display. Since the first and the third information content are not illustrated or provided simultaneously the respective information can be provided on one and the same or on overlapping areas of the electronic display.

With other examples and wherein the third information content is of the second information type respective first and third information contents may be also provided simultaneously and hence spatially non-overlapping on the electronic display. Then, the electronic display is capable to visualize or to display at least two different types of information simultaneously on the electronic display. When the processor is configured to visualize or to display the first and the third information content separately, e.g. sequentially or alternately on the electronic display, respective first and third information contents, each of which representing different types of information, may be presented and illustrated in the same or in spatially overlapping areas of the electronic display.

In an alternative approach of the electronic label the processor is configured to visualize or to display at least a portion of the second information content and at least a portion of the third information content separately, simultaneously, sequentially or alternately on the electronic display. The processor may be configured to visualize or to display only information content of the second information type, thus avoiding illustrating information content of the first information type. This might be of particular use, when the first information type is a rather static information that does not require a modification or reconfiguration during use of the drug delivery device.

By visualizing at least a portion of the second information content and at least a portion of the third information content separately, simultaneously, sequentially or alternately on the electronic display information contents of the first information type and information contents of the second information type can be visualized or displayed simultaneously or sequentially or alternately, namely when the third information content is of the second information type. With other configurations, in which the third information content is of the second information type, the electronic label may be limited to visualize or to display different information contents of the second information type either separately, simultaneously, sequentially or alternately on the electronic display.

With either implementation the electronic label can be reconfigured in accordance to medicament-specific, device-specific or user-specific demands.

According to a further example the electronic label further includes a data storage connected to the processor or integrated into the processor. The data storage is a digital data storage. The data storage is configured to store numerous information contents of the first information type and to store numerous information contents of the second information type. There may be provided storage space for a rather large amount of information contents, either of the first type or the second type. The data storage may be implemented as a non-volatile data storage. The data storage may include memory blocks of read only memory type (ROM). The data storage may further include memory blocks of erasable programmable read-only memory type (EPROM). With some examples the information contents of the first information type are stored in ROM memory blocks. With some examples the information content of the second information type is stored in EPROM memory blocks. Insofar, the information content of the first information type may be stored in the data storage without being changed. The information content of the second information type may be erased or modified by the processor. In particular, the information contents of the second information type may represent reconfigurable information being subject to dynamic changes as the electronic label and/or the drug delivery device are in use.

According to a further example the first information type includes generic information about the medicament. Typically, the first information type is limited to generic information about the medicament. The first information type may include information such as a drug name, a LOT number, a production date, a production site, a suitable storage temperature, a volume of a drug container, a concentration of an active ingredient and a best before date. The above listed information contents are non-limiting and the information content of the first information type may include further information that characterizes the medicament or drug being located inside the drug delivery device or being intended to be used with the drug delivery device. In particular, the first information type may include regulatory information about the proper use of the medicament located inside the drug delivery device.

According to a further example the second information type includes information about a momentary status, about an actual use or about a prior use of the drug delivery device. In particular, the second information type is characteristic of a handling of the drug delivery device and/or of the intended use and purpose of the medicament to be administered by the drug delivery device. Typically, the second information type includes information contents such as a battery level of the electronic label, user instructions, such as “remove cap”, “set a dose of a particular size”, “inject a dose”, time information about injection of the last or previous dose, time information indicating when the next dose injection will be due, information about a remaining content of the drug in the container, an indication that a dose injection took place or has terminated as well as further instructions and information to a user, such as to wait for a certain time interval before removing a needle from an injection site when administering a dose of the medicament by way of injection into biological tissue.

Since the electronic label is provided with two different types of information the respective information types can be processed and illustrated on the electronic display in close correspondence to typical and characteristic scenarios of use. For instance, when the electronic label is attached to the drug delivery device and when the drug delivery device is not in use, the electronic label may be configured to illustrate only a minimum of, e.g. regulatory information, thereby illustrating only a limited amount of information content of the first information type. For instance, in a default or idle mode, the electronic label may be configured to illustrate only a name of a medicament located inside the drug delivery device. It is then only upon use or upon a wake up of the processor, that the electronic display is provided with a further information content, e.g. of the first information type and/or of the second information type in order to assist and/or to instruct a user for setting and/or administering a dose of the medicament.

According to a further example the electronic label includes a clock generator. The clock generator is connected to or is integrated in the processor. The processor is configured to visualize or to display at least a portion of one of the first information content and the second information content during a predefined time interval. After lapse of the predefined time interval the processor is configured to switch or to modify the visual appearance of the electronic display. Typically, and after lapse of the predefined time interval the processor is configured to visualize or to display at least a portion of the third information content. The third information content is either of the first information type or of the second information type.

With some examples, the third information content is displayed or visualized instead of the first information content after lapse of the predefined time interval.

Typically and according to further examples the third information content may be also visualized, displayed or illustrated for a further predefined time interval. After lapse of the further predefined time interval the processor is configured to visualize or to display at least a portion of a fourth information content, wherein the fourth information content is of the first information type or of the second information type. The time interval and the further time interval may be of equal or of different duration.

After lapse of the further predefined time interval the processor may be configured to visualize or to display again at least a portion of one of the first information content and the second information content. Hence, the processor may be configured to visualize or to display different display contents in a loop. Hence, the processor may be configured to visualize or to display a first display configuration for a first predefined time interval. After lapse of the first predefined time interval the processor may switch to a second display configuration. The second display configuration may be illustrated during a second predefined time interval. Thereafter, the processor may be configured to autonomously switch the electronic display to visualize or to display a third display configuration and so on. After illustrating a sequence of different display configurations the processor may be configured to switch back to the first display configuration to start or to re-start the loop of numerous different display configurations from the beginning.

Here, the processor may be configured to switch the display configuration in accordance to given regulatory demands. When switching between different display configurations a portion of the information content visualized or displayed during a first display configuration may be also included in the second display configuration and so on. Insofar, the processor may be configured to permanently illustrate, e.g. at least a portion of the first information type. By switching between a first and a second display configuration the portion of the first information type may remain unaltered, whereas another portion of the display, e.g. illustrating a first or second information content is subject to a visible change.

As an example, the medicament name may be permanently presented on the display even when the electronic display is switched from a first configuration into a second configuration. By switching the display from the first configuration to the second configuration a further information content simultaneously illustrated with the medicament name may be subject to a visible change. For instance, the further information content visualized or displayed concurrently with the medicament name may switch from an information content such as “time of last dose” to another information content, such as “next dose due”.

According to another example the processor is configured to switch the electronic display between an idle mode and an activated mode. When in the idle mode, the electronic display consumes less electric energy compared to when in the activated mode. Here, the processor may be configured to autonomously switch the electronic display from the activated mode into the idle mode, typically after lapse of a predefined time interval. Moreover, the processor may be connected to an input, to a sensor or may communicate with an external electronic device. When and as long as in the activated mode the processor may be configured to monitor a user-induced actuation of a user input, to monitor electronic signals of a sensor, such as an onboard ambient sensor or to monitor communication with an external electronic device, such as a handheld external electronic device, e.g. implemented as a smartphone, tablet computer or smart watch.

In situations, in which the processor does not detect an input during a predetermined time interval this is a clear indication that the electronic label and/or the drug delivery device is currently not in use. For the purpose of saving electric energy the processor is then configured to autonomously switch the electronic display from the activated mode into the idle mode. When switching into the idle mode, the brightness of the electronic display may be reduced compared to the activated mode. Moreover, the information density and/or the amount of information on the electronic display may be reduced when the electronic display is switched from the activated mode into the idle mode.

The processor may be further configured to switch the electronic display from the idle mode back into the activated mode, e.g. when detecting at least one of a user input, a sensor output or a communication and/or data exchange with an external electronic device. By any of these actions, that may be user-induced, the sensor and/or the electronic display may wake up and provide predefined visual information to the user on the electronic display.

According to a further example the electronic label includes at least one ambient sensor. The ambient sensor is connected to the processor. The ambient sensor is further configured to determine at least one of an ambient brightness, a magnetic field, an acceleration, an orientation, a temperature and a variation of ambient air pressure. Here, the processor is configured to visualize, to display and/or to modify at least a portion of one of the first information content and the second information content on the electronic display when receiving a sensor signal, e.g. an electronic signal from the ambient sensor.

When implemented as a magnetic field sensor and/or when implemented as an acceleration sensor, the ambient sensor is configured to monitor or to detect a movement and/or an orientation of the electronic level with regard to the field of gravity. When for instance the ambient sensor detects an initial movement after a rather long time period during which no movement was detected this is a clear indication, that a user picks up the drug delivery device to which the electronic label is attached to. By detecting a sensor signal being indicative of a movement or acceleration of the electronic label and/or of the drug delivery device the processor is configured to switch the electronic display from the idle mode into the activated mode. Moreover, upon detection of a movement the electronic label may provide at least a portion of the second information content of the second information type. Moreover, in accordance to predefined time intervals and/or in accordance to further sensor signals the processor may be configured to provide a sequence of information contents of the second information type being indicative of numerous sequential steps for an intended handling of the drug delivery device. In this way, the electronic label may assist a user in setting and administering of a dose of the medicament.

Instead or in addition to an acceleration sensor the ambient sensor may be equipped with an air pressure sensor that may be equally used to detect or to quantitatively determine a movement of the electronic label and/or of the drug delivery device to which the electronic label is attached to.

According to a further example the processor is operable to turn or to flip an orientation of at least one of the first information content and the second information content depending on an electric signal received from the ambient sensor. This functionality of the processor particularly applies, wherein the ambient sensor is one of a magnetic field sensor, an acceleration sensor and an air pressure sensor. With these types of sensors, an orientation of the electronic label relative to the field of gravity can be determined. In accordance to an orientation of the electronic display relative to the field of gravity the processor is operable to switch or to flip the orientation of at least one of the first information content and the second information content. Typically, the processor is configured to flip or to reorient the entirety of the content of the electronic display in accordance to the orientation of the electronic label relative to the field of gravity.

In this way, a visual appearance of numerous information contents, either of the first information type and/or of the second information type can be dynamically adapted to the momentary orientation of the electronic label and/or of the injection device. In this way it is substantially guaranteed that the label, in particular its information content is readable in either available or conceivable orientation of the label.

According to another example the electronic label includes at least one input connected to the processor and actuatable by a user of the drug delivery device. Here, the processor is configured to modify the visual appearance of the electronic display upon actuation of the at least one input. The input may be provided as a touch-sensitive area on the electronic display.

With other examples the input is provided as a separate button on an upper surface of the flexible substrate outside the area of the electronic display. Moreover, and when the electronic display is configured to communicate with an external electronic device, the input can be also provided via the external electronic device. This particularly applies, when the external electronic device has paired with the electronic label, e.g. when the external electronic device has established a data link, e.g. a wireless data link with the electronic label. Non limiting examples of wireless data links include: BlueTooth, Bluetooth Low Energy (BLE), WIFI, IEEE802.11, and various radio frequency based communication standards, such as RFID or Near Field Communication (NFC).

In this way a user is given the control to modify the visual appearance of the electronic display on demand. For instance, by actuating of the input the user may trigger switching of the electronic label, in particular of its electronic display from the idle mode into the activated mode. Moreover, the user may induce switching the electronic display from the activated mode into the idle mode. A duration of actuation, e.g. a duration of depressing of an input may trigger different switching scenarios or switching directions. For instance, a rather short actuation of the input may temporally increase brightness of the electronic display and may be further used to trigger switching of the display from the idle mode into the activated mode. A rather long actuation or depressing of the input may be interpreted by the processor to switch the electronic display into the idle mode, e.g. for the purpose of saving electric energy.

The input and the processor may be further configured to trigger switching from a first display configuration into a second display configuration. In this way a user is given the possibility to trigger displaying of a sequence of different information contents, either of the first information type and/or of the second information type.

According to another example the electronic label includes a battery connectable to the processor. With some examples the battery may be permanently connected to the processor. The processor is configured to determine or to measure a charging level of the battery. The processor is further operable to switch the electronic display into a power saving mode, when the charging level of the battery drops below a predefined minimum. When in the power saving mode, the brightness of the display may be reduced per default. Moreover, in the power saving mode it is even conceivable, that the electronic display is at least temporally switched off. For instance, the display can be switched off during predefined time intervals in order to save electric power or energy.

With some examples the power saving mode may be even activated during looped illustration of various information contents, hence during an alternating switching between different information contents. Here, between successive and different display configurations, the display may be temporally switched off.

In the power saving mode, the processor and the display may be configured to visually illustrate to a user that the electronic label runs out of power. With some examples, and when in the power saving mode, the electronic label may be configured to autonomously deactivate rather power consuming functions.

In the power saving mode the processor and the electronic display may be further configured to show a display configuration that prompts a user to exchange the electronic label, to charge the battery or to exchange the battery.

According to a further example the electronic label includes a planar-shaped warning buzzer connected to the processor. The warning buzzer is configured to generate an audible sound when activated by the processor. The processor may be configured to detect or to identify numerous warning or alert situations, e.g. when a dose currently set is larger than a prescribed dose, when a battery is going to run out of electric power, when setting and/or injecting of a next dose is currently overdue or the like. The warning buzzer is configured to become activated by the processor in response to the detection or identification of an alert. The warning buzzer may be planar-shaped and may include a limited height on the flexible substrate. The warning buzzer may include a piezoelectric transducer configured to generate an audible warning when activated by the processor. The thickness or height of the warning buzzer may be smaller than 5 mm, smaller than 3 mm or even smaller than 2 mm along a direction parallel to the surface normal of the substrate.

According to a further example the electronic display is one of an electroluminescent display, an electrophoretic display, a liquid crystal display and a light emitting diode (LED) display. When implemented as a light emitting diode display the display may include an organic light emitting diode (OLED) display. Such OLED displays can be bendable type and are suitable to be used with the flexible substrate. Hence, the electronic display may include a flexible sheet display. The electronic display may include numerous display layers that are flexible. The electronic display may include flexible display layers that are stacked on top of each other.

With other examples and when implementing the electronic display as an electrophoretic display the display enables to provide a persistent and durable display configuration and a respective information content on the electronic display even if the electronic label should be insufficiently supplied with electric energy. Here, only switching of the electronic display between different display configurations consumes electric power or electric energy. An electrophoretic display is particularly suitable for scenarios of use, wherein the electronic label should provide a rather long lifetime that may exceed several months or years.

Implementing the electronic display as a light emitting diode display provides excellent contrast readability and brightness. Moreover, light emitting diode display can be provided with a comparatively high resolution, such as more than 50 pixels per inch (PPI), more than 70 ppi, more than 100 ppi, more than 120 ppi, more than 140 ppi or even more than 150 PPI.

According to another example the electronic display includes a color display configured to visualize or to display at least one of the second information content and an information background in at least two different colors. Hence, the electronic display is a color display. With further examples, the electronic display is configured to modify the brightness of at least one of the first and/or information contents and an information background.

With some examples the electronic label includes at least one device sensor. The device sensor is configured to determine at least one of a position or orientation of at least one of a dose tracker and a piston rod of an injection device relative to a housing or body of the injection device, when the electronic label is attached to the injection device.

According to another example the device sensor of the label includes an electrode structure on the substrate. The electrode structure is configured to measure at least one of an electric capacitance, an electric field and a magnetic field. Typically, the drug delivery device is equipped with and/or includes a dose tracker the position or orientation of which in relation to the housing or body of the drug delivery device is indicative of a size of a dose currently set or dispensed. The dose tracker may be provided with an electronically, electrically and/or magnetically detectable feature. In this way, the device sensor with its electrode structure is configured and/or operable to determine a position and/or orientation of the dose tracker of the drug delivery device during handling and operation of the injection device for setting and/or dispensing of a dose of the medicament.

The device sensor may be a contactless sensor. The electrode structure may be embedded in the flexible substrate. The electrode structure may be arranged on an upper side of the flexible substrate. A lower side of the flexible substrate may be provided with an adhesive for attaching the flexible substrate and hence the label to the body. The electrode structure for measuring at least one of an electric capacitance, an electric field and a magnetic field enables a contactless determination and/or quantitative measuring of a position or orientation of the dose tracker of the injection device relative to a housing or body of the drug delivery device when the label is attached to the drug delivery device.

According to a further example the electronic display includes at least one electrically conductive grid electrode at least partially spatially overlapping with the electrode structure of the device sensor. The at least one electrically conductive grid electrode provides an electromagnetic shield for the electrode structure of the device sensor. This is of particular advantage when the electrode structure is susceptible to ambient electric or electromagnetic fields. Here, the conductive grid electrode of the electronic display may provide a double function. The conductive grid electrode may be operable to drive and/or to operate the electronic display. At the same time, the electrically conductive grid electrode serves to screen and/or to shield the electrode structure of the device sensor that is typically located underneath.

In a layer stack of the label the electrode structure of the device sensor is provided on an upper side of the flexible substrate. Typically, the at least one electrically conductive grid electrode is arranged on top of the electrode structure of the device sensor. Hence, the electrode structure of the device sensor is located between the flexible substrate and the at least one electrically conductive grid electrode.

With other examples, the electrode structure of the device sensor is located or arranged on a lower side of the flexible substrate. Then, the at least one electrically conductive grid electrode is located on an upper side or outside facing portion of the flexible substrate. In either way, the electrode structure of the device sensor is effectively shielded against ambient electromagnetic or electrostatic perturbations.

The flexible substrate is particularly configured to wrap around at least a portion of the body or housing of the injection device. The body or housing may include a somewhat cylindrical or tubular structure. The flexible substrate may hence conform or customize to a sidewall of the tubular shaped housing of the injection device. The flexible substrate enables a rather universal attachment of the label to a multitude of different injection devices. The label may be universally applicable and/or attachable to different types of injection devices.

The label is also rather thin or flat and can be permanently attached to the housing of the injection device. The injection device with the label attached thereto can be wrapped or packed in a device packaging, e.g. for transportation and/or storage. If at all, the label only has a minor impact on the outer contour and/or geometry of the injection device when attached to the housing of the injection device. The label may further impart a rather attractive design to the injection device.

The flexible substrate may include a flexible plastic foil or a flexible metal foil. The flexible substrate may include a plastic foil e.g. made of polyethylene (PE) or polyethylene terephthalate (PET).

The flexible substrate, the electronic display and hence the entire label may include a total thickness of less than 5 mm, less than 4 mm, less than 3 mm or less than 2 mm. With some examples the label includes a thickness of less than 1 mm or less than 0.5 mm.

Typically, and with numerous examples the label includes an electronic circuit located on the substrate. The electronic circuit is electrically connected to the processor and to the electronic display. The electronic circuit may be directly arranged on the flexible substrate. The electronic display and/or the processor may be integrated into the electronic circuit.

The electronic circuit may include a flexible electronic circuit. Hence, electrically conductive structures of the electronic circuit are bendable or pliable so as to follow a flexible deformation of the substrate, e.g. in the course of attaching the flexible substrate to the housing of the injection device, e.g. through wrapping the label to the tubular shaped housing.

The electronic circuit may be printed on the substrate. The electronic circuit may be printed on the flexible substrate by one or more inks that are composed of carbon-based compounds. Moreover, the electronic circuit may be deposited on the flexible substrate by a solution-based or vapor-based deposition process. A printed electronic circuit on the substrate enables a low cost volume fabrication of the label.

In another example a lower side of the flexible substrate is at least in sections provided with an adhesive. The lower side of the flexible substrate may be provided with an adhesive layer. The entire lower side of the flexible substrate or only portions thereof may be provided with the adhesive. Especially the border regions of the lower side of the flexible substrate are provided with the adhesive in order to enable a permanent attachment of the label to the housing of the injection device. By means of the adhesive on the lower side of the flexible substrate an adhesion-based fixing of the label to a body or housing of the injection device or adapted can be provided. This is rather space saving and can be implemented at moderate or low cost.

According to another example the electronic circuit further includes a battery. The battery is typically connected to the processor and/or to the electronic display. The processor and/or the battery may be printed on the flexible substrate. The processor and/or the battery may also be flexible to a certain degree thus allowing and supporting a deformation of the flexible substrate upon assembly and attachment to the housing of the injection device.

The processor is connected to the electronic display and is also connected to the battery. The processor is driven by electric energy provided by the battery. Typically, both the processor and the battery include or are made of printed electronic components.

With further examples the electronic circuit includes a data storage or memory configured to store at least one of a number of user activities and a point of time of a user activity or of numerous user activities. In combination with a clock of the processor a time indication can be derived thus enabling storage of a point of time of a user activity, e.g. a point of time at which a user actuates, e.g. touches or depresses an input of the label. If the label is void of a clock the electronic circuit may be simply configured to count a number of such user activities. In this way, a kind of a dosage counter can be provided by the label.

According to another example the electronic circuit includes an antenna for wireless transmission of electronic signals with an external electronic device. The antenna is typically connected to the processor. By means of the antenna the processor is configured to communicate with an external electronic device. The processor may be configured to transmit data to the external electronic device. The processor may be configured to receive data from the external electronic device. The external electronic device may include a handheld external electronic device, such as a smartphone, a smart watch or a tablet computer. The antenna may be further enabled to provide communication with a personal computer or similar computing devices.

The antenna and its interaction with the processor further enables a transfer of data previously stored in the data storage of the electronic circuit to the external electronic device. By means of the antenna the external electronic device may be configured to read out the content of the data storage of the label. Typically, the data storage is integrated into the electronic circuit. With other examples it may be provided separately, hence offset from the electronic circuit. The wireless transmission of electronic signals between the processor and the external electronic device further enables a reconfiguring of the processor and/or of the electronic display.

With the external electronic device and the wireless transmission of electronic signals the external electronic device may be used to reconfigure the label. In this way, the at least one indication may be replaced by a second indication. In addition, the total appearance of the electronic display may be reconfigured in accordance to electronic signals received from the external electronic device. In this way, the at least one electronic display can be individually configured for different usage scenarios and/or for use with different injection devices.

The transmission of data stored in the data storage of the electronic circuit to the external electronic device enables a monitoring and post-dispensing evaluation of user activities that were recorded in the data storage at during time intervals during which the label is disconnected from the external electronic device.

Even though the label as described herein may be particularly configured for attachment to an injection device the label may be equally attachable to a body of some other or further medical device, such as an infusion device, an infusion pump, an injection pump, an inhaler, or a portable medical analysis device, such as a blood glucose meter. Insofar, any reference to an injection device may be regarded as a reference to a respective medical device, respectively.

According to another aspect the disclosure also relates to a drug delivery device for administering a medicament to a patient. The drug delivery device may be configured to administer, e.g. to inject an injectable medicament by setting and dispensing of a dose of the medicament to a patient. The drug delivery device may be configured as a handheld injection device, such as a handheld pen-type injector or as a medicament pump. The drug delivery device includes a housing. The housing includes or constitutes a body. The housing is configured to accommodate a medicament container filled with the medicament to be administered. The drug delivery device further includes a drive mechanism configured to withdraw or to expel a dose of the medicament from the medicament container.

The drive mechanism is further configured to administer the dose of the medicament to a patient. Moreover, the drug delivery device is provided with a label as described above. The label is attached to the housing or to the body of the drug delivery device. The body of the delivery device is part of the housing of the delivery device. It may be or may constitute a proximal part of the housing of the drug delivery device that is located at an end of the delivery device facing away from a medicament outlet or from a dispensing end of the drug delivery device.

With some examples and when the drug delivery device is implemented as an injection device the drive mechanism includes a piston rod displaceable along a longitudinal direction. The longitudinal direction may coincide or may extend parallel to a longitudinal axis of the housing of the injection device. The piston rod is configured to operably engage with a piston of a medicament container. The medicament container may be implemented as a cartridge sealed in proximal direction by the piston. The cartridge contains the injectable medicament. A distal end of the cartridge located opposite to the piston rod is provided with a pierceable seal that is typically penetrable by a double-tipped injection needle.

With further examples, the disclosure relates to a medical device, such as an infusion device, an infusion pump, an injection pump, an inhaler, or a portable medical analysis device, such as a blood glucose meter. The medical device is further provided with an electronic label as described above. The label is attached to the housing or to a body of the medical device. The body of the medical device may be part of the housing of the respective medical device.

According to a further example the medicament container, e.g. in form of a cartridge containing the medicament is arranged inside the housing of the injection device. The injection device may be configured as a disposable injection device. The medicament container filled with the medicament may be readily assembled inside the injection device as the injection device is handed out to customers or patients.

The injection device may be implemented as a disposable injection device intended and/or configured to be discarded in its entirety after use and/or when the medicament has been used up or has exceeded its best before date. With other examples the injection device is implemented as a reusable injection device, wherein a medicament cartridge or medicament container filled with the medicament can be exchanged and replaced.

With some examples the injection device is a fixed dose injection device providing setting and injecting only one of a predefined dose size. With other examples the injection device is implemented as a variable dose injection device, wherein a user may individually set doses of different sizes for injection.

In a further aspect the disclosure also relates to an adapter configured for a releasable attachment to a housing of an injection device. The adapter includes a rigid body comprising an outside surface and comprising a counter fastening feature configured to releasably mechanically engage with a correspondingly or complementary shaped fastening feature of the housing of the injection device. The adapter further includes an electronic label as described above that is attached to the outside surface of the rigid body. Here, the injection device itself may be void of a label as described above. The injection device may include only a conventionally printed label.

With some examples the rigid body includes a tubular-shaped sleeve configured to receive at least a portion of the housing of the injection device inside the sleeve. The label may be adhesively attached to the outside surface of the rigid body. The label can be prefixed to the outside surface of the rigid body. It is fixed and attached to the rigid adapted body in a well-defined position and/or orientation. The adapter provided with the label on its outside surface is particularly configured to retrofit existing injection devices with a label without the necessity to e.g. adhesively attach the label to the injection device.

With numerous examples and when the label is equipped with a device sensor it may be important that the label is correctly and/or precisely attached and fixed in a well-defined position and/orientation relative to the housing of the injection device. This can be provided with the counter fastening feature of the rigid body configured to engage with the fastening feature of the injection device.

The fastening feature may include at least one of a radial protrusion or radial recess to engage with a correspondingly shaped radial recess or radial protrusion of the counter fastening feature. The fastening feature and the counter fastening feature may be implemented as mutually corresponding snap features. Moreover, only one of the counter fastening feature and the fastening feature may be implemented as a snap feature whereas the other one of the counter fastening feature and the fastening feature is implemented as a raised ridge or groove on the outside of the housing of the injection device or on the inside of the rigid body of the adapter.

With a further example the rigid body of the adapter includes a cap fastening feature configured for engagement with a protective cap of the injection device. This is of particular benefit when the fastening feature of the housing of the injection device is implemented as a cap fastening feature configured to engage with a counter fastening feature of the protective cap of the injection device. The cap fastening feature of the housing of the injection device may be originally configured for a releasable attachment and/or releasable fixing of a protective cap of the injection device, e.g. covering a distal end of the housing of the injection device.

The counter fastening feature of the rigid body may mimic or replace the counter fastening feature of the protective cap of the injection device. The counter fastening feature of the rigid body may engage with the fastening feature of the housing of the injection device instead of the fastening feature of the protective cap. The rigid body, e.g. implemented as a tubular shaped sleeve may be adapted to receive a proximal housing portion of the injection device in such a way, that the counter fastening feature of the rigid body is located at a distal end of the rigid body. Then, the distal end of the rigid body may be provided with a cap fastening feature to engage with a counter fastening feature of the protective cap. Here, the protective cap originally supplied with the injection device may be replaced by another protective cap configured for engagement with the rigid body of the adapter when the adapter is engaged with the fastening feature of the housing of the injection device.

According to another aspect the present disclosure also relates to a method of visualizing a first information content of a first information type and visualizing a second information content of a second information type on an electronic display of an electronic label as described above. The method includes the steps of visualizing at least a portion of the first information content of the first information type on the electronic display and separately, simultaneously, sequentially or alternately visualizing at least a portion of a third information content on the electronic display. Here, the third information content is of the first information type or of the second information type.

In particular, the method of visualizing first and second information contents on the electronic display of the electronic label is closely or directly correlated to the use of the electronic label as described above. Insofar, the features, effects and benefits obtainable by the electronic label and the drug delivery device as described above equally apply to the method of visualizing first and second information contents; and vice versa.

In the present context the term 'distal' or 'distal end' relates to an end of the injection device that faces towards an injection site of a person or of an animal. The term 'proximal' or 'proximal end' relates to an opposite end of the injection device, which is furthest away from an injection site of a person or of an animal.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codeable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide. Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrom.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not include a full-length antibody polypeptide, but that still includes at least a portion of a full-length antibody polypeptide that is capable of binding to an antigen. Antibody fragments can include a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelid antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

BRIEF DESCRIPTION OF THE FIGURES

In the following, numerous examples of an electronic label without and in in combination with a drug delivery device will be described in greater detail by making reference to the drawings, in which:

FIG. 3 shows the injection device of FIG. 1 with an electronic sensitive label attached to the housing of the injection device.

Like reference numbers indicate like elements.

DETAILED DESCRIPTION

Figure 1:
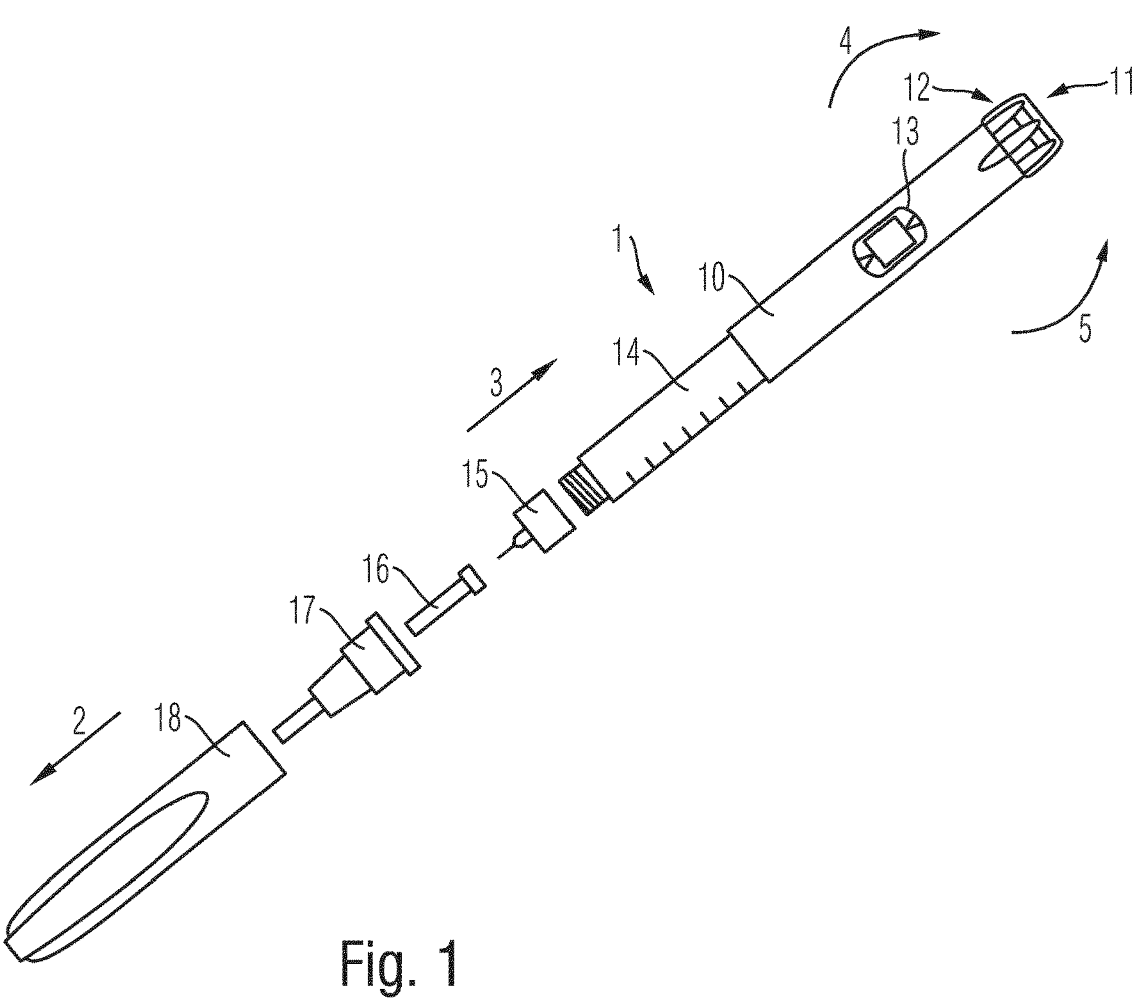
FIG. 1 shows an example of an injection device.
Figure 2:
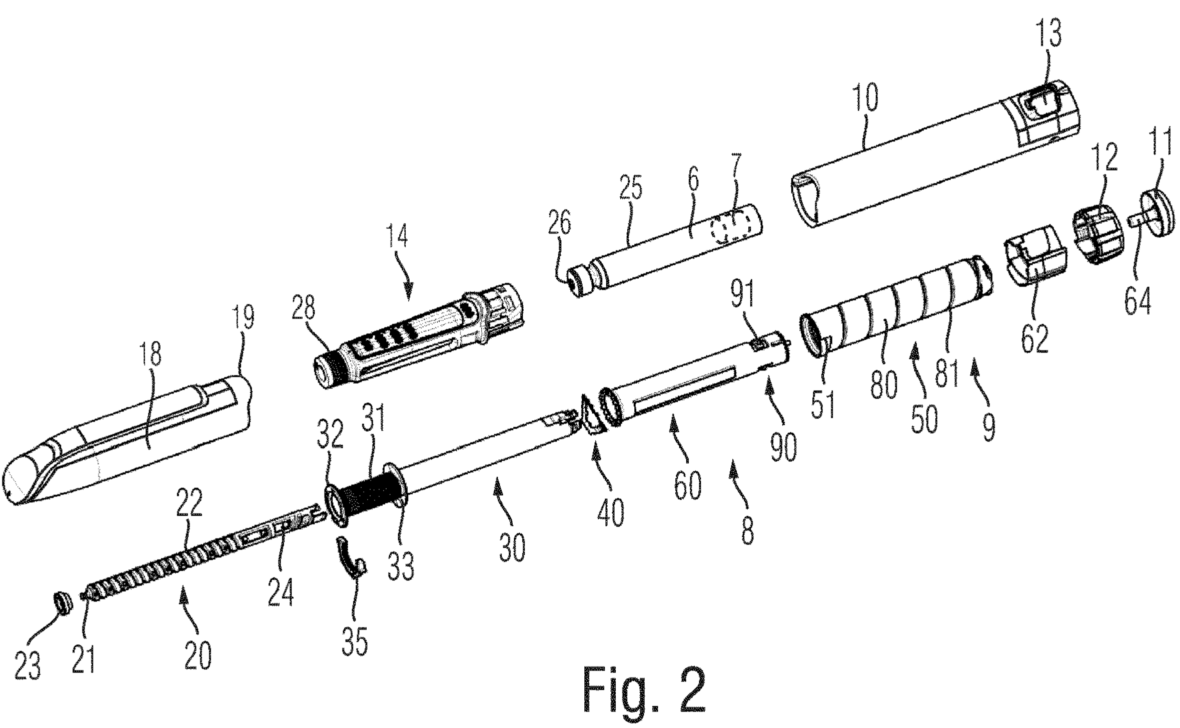
FIG. 2 shows the injection device of FIG. 1 in an exploded perspective view.

The injection device 1 as shown in FIGS. 1 and 2 is a pre-filled disposable injection device that includes a housing to which an injection needle 15 can be affixed. The injection needle 15 is protected by an inner needle cap 16 and either an outer needle cap 17 or a protective cap 18 that is configured to enclose and to protect a distal section of the housing of the injection device 1. The housing typically includes a body 10 that forms at least a main housing part configured to accommodate a drive mechanism 8 as shown in FIG. 2. The injection device 1 may further include a distal housing component denoted as cartridge holder 14. The cartridge holder 14 may be permanently or releasably connected to the body 10. The cartridge holder 14 is typically configured to accommodate a cartridge 6 that is filled with a liquid medicament. The cartridge 6 includes a cylindrically-shaped or tubular-shaped barrel 25 sealed in proximal direction 3 by means of a bung 7 located inside the barrel 25. The bung 7 is displaceable relative to the barrel 25 of the cartridge 6 in a distal direction 2 by means of a piston rod 20. A distal end of the cartridge 6 is sealed by a pierceable seal 26 configured as a septum and being pierceable by a proximally directed tipped end of the injection needle 15. The cartridge holder 14 includes a threaded socket 28 at its distal end to threadedly engage with a correspondingly threaded portion of the injection needle 15. By attaching the injection needle 15 to the distal end of the cartridge holder 14 the seal 26 of the cartridge 6 is penetrated thereby establishing a fluid transferring access to the interior of the cartridge 6.

When the injection device 1 is configured to administer e.g. human insulin, the dosage set by a dose dial 12 at a proximal end of the injection device 1 may be displayed in so-called international units (IU, wherein 1 IU is the biological equivalent of about 45.5 μg of pure crystalline insulin (1/22 mg). The dose dial 12 may include or may form a dose dial.

As shown further in FIGS. 1 and 2, the housing 10 includes a dosage window 13 that may be in the form of an aperture in the housing 10. The dosage window 13 permits a user to view a limited portion of a number sleeve 80 that is configured to move when the dose dial 12 is turned, to provide a visual indication of a currently set dose. The dose dial 12 is rotated on a helical path with respect to the housing 10 when turned during setting and/or dispensing or expelling of a dose.

The injection device 1 may be configured so that turning the dosage knob 12 causes a mechanical click sound to provide acoustical feedback to a user. The number sleeve 80 mechanically interacts with a piston in the insulin cartridge 6. When the needle 15 is stuck into a skin portion of a patient, and when the trigger 11 or injection button is pushed, the insulin dose displayed in display window 13 will be ejected from injection device 1. When the needle 15 of the injection device 1 remains for a certain time in the skin portion after the trigger 11 is pushed, a high percentage of the dose is actually injected into the patient's body. Ejection of an insulin dose may also cause a mechanical click sound, which is however different from the sounds produced when using the dose dial 12.

In this embodiment, during delivery of the insulin dose, the dose dial 12 is turned to its initial position in an axial movement, that is to say without rotation, while the number sleeve 80 is rotated to return to its initial position, e.g. to display a dose of zero units.

The injection device 1 may be used for several injection processes until either the cartridge 6 is empty or the expiration date of the medicament in the injection device 1 (e.g. 28 days after the first use) is reached.

Furthermore, before using injection device 1 for the first time, it may be necessary to perform a so-called "prime shot" to remove air from the cartridge 6 and the needle 15, for instance by selecting two units of the medicament and pressing trigger 11 while holding the injection device 1 with the needle 15 upwards. For simplicity of presentation, in the following, it will be assumed that the ejected amounts substantially correspond to the injected doses, so that, for instance the amount of medicament ejected from the injection device 1 is equal to the dose received by the user.

An example of the drive mechanism 8 is illustrated in more detail in FIG. 2. It includes numerous mechanically interacting components. A flange like support of the body 10 includes a threaded axial through opening threadedly engaged with a first thread or distal thread 22 of the piston rod 20. The distal end of the piston rod 20 includes a bearing 21 on which a pressure foot 23 is free to rotate with the longitudinal axis of the piston rod 20 as an axis of rotation. The pressure foot 23 is configured to axially abut against a proximally facing thrust receiving face of the bung 7 of the cartridge 6. During a dispensing action the piston rod 20 rotates relative to the housing 10 thereby experiencing a distally directed advancing motion relative to the body 10 and hence relative to the barrel 25 of the cartridge 6. As a consequence, the bung 7 of the cartridge 6 is displaced in distal direction 2 by a well-defined distance due to the threaded engagement of the piston rod 20 with the body 10.

The piston rod 20 is further provided with a second thread 24 at its proximal end. The distal thread 22 and the proximal thread 24 are oppositely handed.

There is further provided a drive sleeve 30 having a hollow interior to receive the piston rod 20. The drive sleeve 30 includes an inner thread threadedly engaged with the proximal thread 24 of the piston rod 20. Moreover, the drive sleeve 30 includes an outer threaded section 31 at its distal end. The threaded section 31 is axially confined between a distal flange portion 32 and another flange portion 33 located at a predefined axial distance from the distal flange portion 32. Between the two flange portions 32, 33 there is provided a last dose limiter 35 in form of a semi-circular nut having an internal thread mating the threaded section 31 of the drive sleeve 30.

The last dose limiter 35 further includes a radial recess or protrusion at its outer circumference to engage with a complementary-shaped recess or protrusion at an inside of the sidewall of the body 10 or housing. In this way the last dose limiter 35 is splined to the body 10. A rotation of the drive sleeve 30 in a dose incrementing direction 4 or clockwise direction during consecutive dose setting procedures leads to an accumulative axial displacement of the last dose limiter 35 relative to the drive sleeve 30. There is further provided an annular spring 40 that is in axial abutment with a proximally facing surface of the flange portion 33. Moreover, there is provided a tubular-shaped clutch 60. At a first end the clutch 60 is provided with a series of circumferentially directed saw teeth. Towards a second opposite end of the clutch 60 there is located a radially inwardly directed flange.

Furthermore, there is provided a dose dial sleeve also denoted as number sleeve 80. The number sleeve 80 is provided outside of the spring 40 and the clutch 60 and is located radially inward of the body 10. A helical groove 81 is provided about an outer surface of the number sleeve 80. The body 10 is provided with the dosage window 13 through which a part of the outer surface of the number 80 can be seen. The body 10 is further provided with a helical rib at an inside sidewall portion of an insert piece 62, which helical rib is to be seated in the helical groove 81 of the number sleeve 80. The tubular shaped insert piece 62 is inserted into the proximal end of the body 10. It is rotationally and axially fixed to the body 10. There are provided first and second stops on the body 10 to limit a dose setting procedure during which the number sleeve 80 is rotated in a helical motion relative to the body 10.

The dose dial 12 in form of a dose dial grip is disposed about an outer surface of the proximal end of the number sleeve 80. An outer diameter of the dose dial 12 typically corresponds to and matches with the outer diameter of the body 10. The dose dial 12 is secured to the number 80 to prevent relative movement there between. The dose dial 12 is provided with a central opening.

The trigger 11, also denoted as dose button is substantially T-shaped. It is provided at a proximal end of the injection device 1. A stem 64 of the trigger 11 extends through the opening in the dose dial 12, through an inner diameter of extensions of the drive sleeve 30 and into a receiving recess at the proximal end of the piston rod 20. The stem 64 is retained for limited axial movement in the drive sleeve 30 and against rotation with respect thereto. A head of the trigger 11 is generally circular. The trigger side wall or skirt extends from a periphery of the head and is further adapted to be seated in a proximally accessible annular recess of the dose dial 12.

To dial a dose a user rotates the dose dial 12. With the spring 40 also acting as a clicker and the clutch 60 engaged, the drive sleeve 30, the spring or clicker 40, the clutch 60 and the number sleeve 80 rotate with the dose dial 12. Audible and tactile feedback of the dose being dialed is provided by the spring 40 and by the clutch 60. Torque is transmitted through saw teeth between the spring 40 and the clutch 60. The helical groove 81 on the number sleeve 80 and a helical groove in the drive sleeve 30 have the same lead. This allows the number sleeve 80 to extend from the body 10 and the drive sleeve 30 to climb the piston rod 20 at the same rate. At a limit of travel a radial stop on the number sleeve 80 engages either with a first stop or a second stop provided on the body 10 to prevent further movement in a first sense of rotation, e.g., in a dose incrementing direction 4. Rotation of the piston rod 20 is prevented due to the opposing directions of the overall and driven threads on the piston rod 20.

The last dose limiter 35 keyed to the body 10 or housing is advanced along the threaded section 31 by the rotation of the drive sleeve 30. When a final dose dispensed position is reached, a radial stop formed on a surface of the last dose limiter 35 abuts a radial stop on the flange portion 33 of the drive sleeve 30, preventing both, the last dose limiter 35 and the drive sleeve 30 from rotating further.

Should a user inadvertently dial beyond the desired dosage, the injection device 1, configured as a pen-injector allows the dosage to be dialed down without dispense of the medicament from the cartridge 6. For this the dose dial 12 is simply counter-rotated. This causes the system to act in reverse. A flexible arm of the spring or clicker 40 then acts as a ratchet preventing the spring 40 from rotating. The torque transmitted through the clutch 60 causes the saw teeth to ride over one another to create the clicks corresponding to dialed dose reduction. Typically, the saw teeth are so disposed that a circumferential extent of each saw tooth corresponds to a unit dose. Here, the clutch may serve as a ratchet mechanism.

As an alternative or in addition the ratchet mechanism 90 may include at least one ratchet feature 91, such as a flexible arm on the sidewall of the tubular-shaped clutch 60. The at least one ratchet feature 91 may include a radially outwardly extending protrusion e.g. on a free end of the flexible arm. The protrusion is configured to engage with a correspondingly shaped counter ratchet structure on an inside of the number sleeve 80. The inside of the number sleeve 80 may include longitudinally shaped grooves or protrusions featuring a saw-tooth profile. During dialing or setting of a dose the ratchet mechanism 90 allows and supports a rotation of the number sleeve 80 relative to the clutch 60 along a second sense of rotation 5, which rotation is accompanied by a regular clicking of the flexible arm of the clutch 60. An angular momentum applied to the number sleeve 80 along the first sense of rotation for is unalterably transferred to the clutch 60. Here, the mutually corresponding ratchet features of the ratchet mechanism 90 provide a torque transmission from the number sleeve 80 to the clutch 60.

When the desired dose has been dialed the user may simply dispense the set dose by depressing the trigger 11. This displaces the clutch 60 axially with respect to the number sleeve 80 causing dog teeth thereof to disengage. However, the clutch 60 remains keyed in rotation to the drive sleeve 30. The number sleeve 80 and the dose dial 12 are now free to rotate in accordance with the helical groove 81.

The axial movement deforms the flexible arm of the spring 40 to ensure the saw teeth cannot be overhauled during dispense. This prevents the drive sleeve 30 from rotating with respect to the housing 10 though it is still free to move axially with respect thereto. The deformation is subsequently used to urge the spring 40 and the clutch 60 back along the drive sleeve 30 to restore the connection between the clutch 60 and the number sleeve 80 when the distally directed dispensing pressure is removed from the trigger 11.

The longitudinal axial movement of the drive sleeve 30 causes the piston rod 20 to rotate through the through opening of the support of the housing 10, thereby to advance the bung 7 in the cartridge 6. Once the dialed dose has been dispensed, the number sleeve 80 is prevented from further rotation by contact of at least one stop extending from the dose dial 12 with at least one corresponding stop of the housing 10. A zero dose position may be determined by the abutment of one of axially extending edges or stops of the number sleeve 80 with at least one or several corresponding stops of the body 10.

In the presently illustrated example, the number sleeve 80 represents a dose tracker 50 being indicative of a size of a dose currently set. Here, the longitudinal and/or rotational position of the dose tracker 50 relative to the housing or body 10 of the injection device 1 is indicative of a size of a currently set. The dose tracker 50 includes a tracking stop feature 51 that is operable to engage with a counter stop of the body 10, e.g. when a zero-dose configuration or when a maximum dose configuration has been reached.

The number sleeve 80 is only one example of a dose tracker 50. Likewise, also the piston rod 20 may act as or may be used as a dose tracker 50.

The expelling mechanism or drive mechanism 8 as described above is only exemplary for one of a plurality of differently configured drive mechanisms that are generally implementable in a disposable pen-injector. The drive mechanism as described above is explained in more detail e.g. in WO2004/078239A1, WO 2004/078240A1 or WO 2004/078241A1 the entirety of which being incorporated herein by reference.

The dose setting mechanism 9 as illustrated in FIG. 2 includes at least the dose dial 12 and the number sleeve 80. As the dose dial 12 is rotated during and for setting of a dose the number sleeve 80 starts to rotate relative to the housing along a helical path as defined by the threaded engagement of its outer thread or helical groove 81 with a correspondingly shaped threaded section at the inside surface of the housing.

During dose setting and when the drive mechanism 8 or the dose setting mechanism 9 is in the dose setting mode the drive sleeve 30 rotates in unison with the dose dial 12 and with the number sleeve 80. The drive sleeve 30 is threadedly engaged with the piston rod 20, which during dose setting is stationary with regard to the housing 10. Accordingly, the drive sleeve 30 is subject to a screwing or helical motion during dose setting. The drive sleeve 30 starts to travel in proximal direction as the dose dial is rotated in a first sense or rotation or in a dose incrementing direction 4, e.g. in a clockwise direction. For adjusting of or correcting a size of a dose the dose dial 12 is rotatable in an opposite second sense of rotation, hence in a dose decrementing direction 5, e.g. counterclockwise.

In FIGS. 3-26 numerous examples of an electronic label 100 configured for attachment to a body 10 of a drug delivery device, presently implemented as an injection device 1 are illustrated. As further indicated in FIGS. 16 and 21 the label 100 may be also configured for attachment to an outside surface 211 of a rigid body 210 of an adapter 200. The adapter 200 is configured to releasably and mechanically engage with a fastening feature 96 of the housing or body 10 of the injection device 1. For this, the adaptor 200 includes a counter-fastening feature 216 correspondingly or complementary-shaped to the fastening feature 96.

Figure 4:
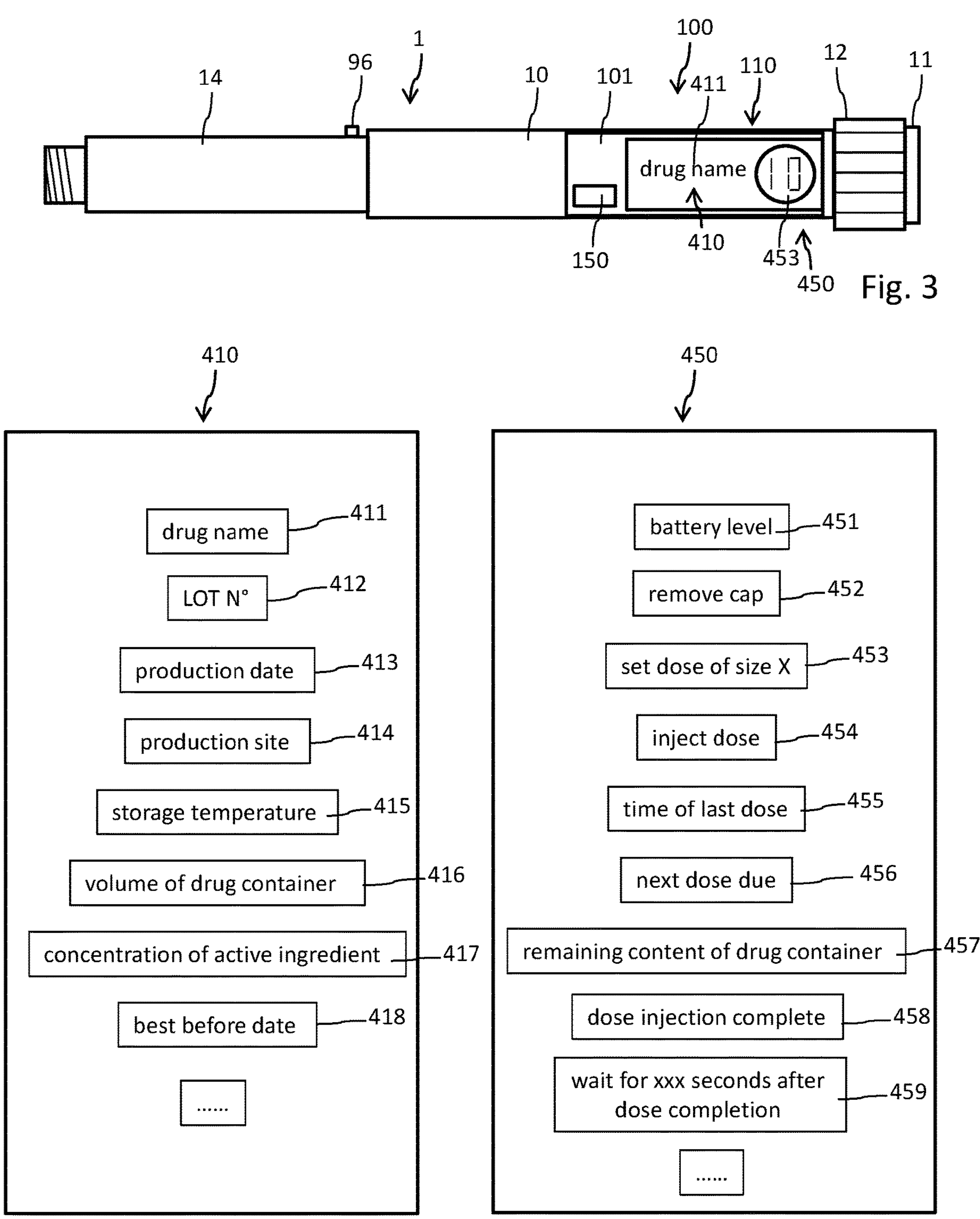
FIG. 4 is illustrative of numerous examples of information contents of first information type and of second information type.
Figure 22:
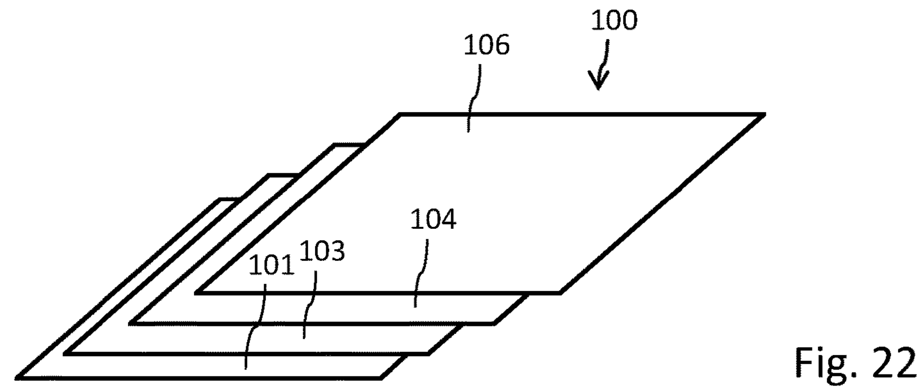
FIG. 22 shows the multilayer structure of the electronic label.

The electronic label 100 includes a flexible substrate 101 as illustrated in FIG. 22. On the flexible substrate 101 there is provided an electronic display 110. The electronic display 110 is a two-dimensional display. The electronic label 100 further includes a processor 140 connected to the electronic display 110 and configured to modify or to control a visual appearance of the electronic display 110. The electronic display 110 is configured to display at least a first information content 411 of a first information type 410 and to display at least a second information content 451 of a second information type 450. The electronic display is further configured to display at least a third information content 412, 452. The third information content 412, 452 is of the first information type 410 or of the second information type 450. In FIG. 4, numerous examples of first, second and third information contents of different, namely of first information type 410 and of second information type 450 are illustrated by way of non-limiting examples.

Figure 24:
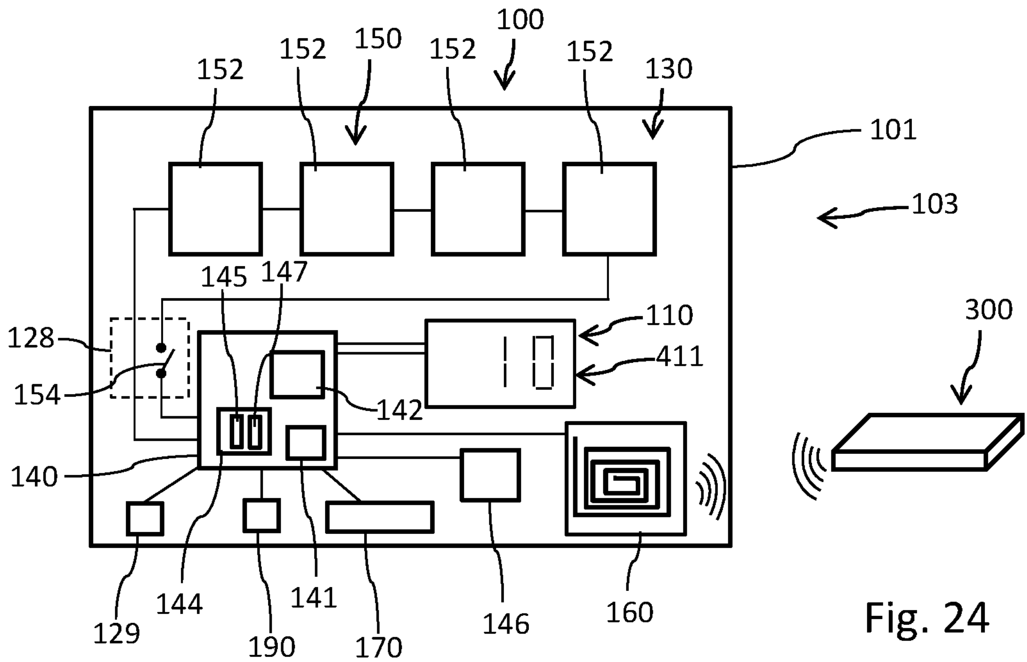
FIG. 24 is a block diagram illustrating the electronic circuit of the electronic label.

The processor 140 as schematically illustrated in the block diagram of FIG. 24 is configured to modify or to control a visual appearance of the electronic display 110 by visualizing at least a portion of the first information content 411 and at least a portion of the third information content 412, 452 separately, simultaneously, sequentially or alternately on the electronic display 110.

Figure 23:
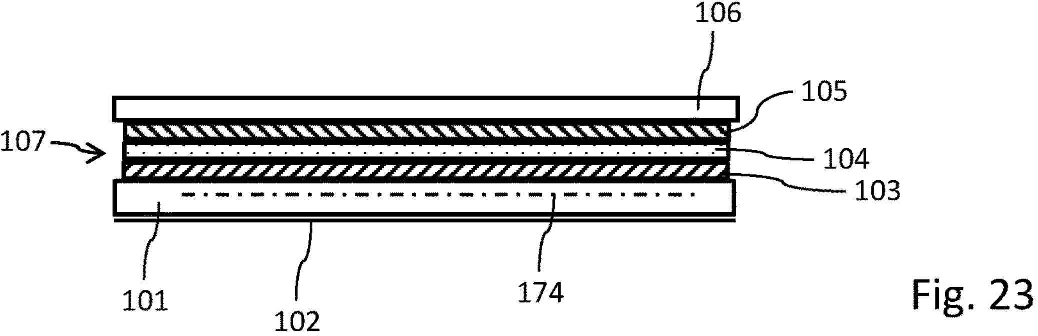
FIG. 23 is a cross-section through an example of the electronic label.

Typically, the electronic display 110 is located on an upper side of the substrate 101. The label 100, at least the electronic display 110 of the label 100 includes a multilayer structure as indicated in FIGS. 22 and 23. The electronic display 110 may thus include a multilayer structure, e.g. a thin film multilayer structure.

The flexible substrate 101 or base substrate may be any material known for producing printed electronic labels, such as PET film or office paper. Other plastic materials are also feasible, e.g. PVC. The base substrate has an adhesive on one side to fix the label to a pen body, e.g. either permanently or removably, depending on the choice of adhesive.

The label 100 may include a mechanically flexible structure. Thus, the label 100 may be bendable or it can wrap around an outer circumference or outside surface of the body 10 of the injection device and/or of a rigid body 210 of the adapter 200, the latter one of which being illustrated in FIGS. 16 and 21.

Hence, the electronic display 110 is a flexible electronic display. It may include one of an electroluminescent display, an electrophoretic display 118, a liquid crystal display and a light emitting diode display 119, in particular an organic light emitting diode display (OLED). Such displays are known to be flexible as well as bendable.

Optionally, the label 100, may be provided with an input 128, e.g. implemented as a touch sensitive area of the electronic display 110. The touch sensitive area or the input 128 may be implemented as a portion of the second label area 110. With some examples the entirety of the electronic display 110 may be implemented as an input area 128 that is touch sensitive. Hence, a touch sensitive area may entirely or at least partially overlap with the electronic display 110. In other words, the electronic display 110 may be implemented as a touch sensitive electronic display 110.

The input 128 is connected to the processor 140. By mechanically engaging, e.g. by touching the input 128 the processor 140 can be prompted to modify or to alter the information content on the electronic display 110. With some examples the input 128 or the touch sensitive area of the electronic display 110 includes capacitive switches produced in printing electronics technology. The input 128 can be implemented as an electrode, which is part of a capacitor. The capacitor can be detuned when an object, such as a finger approaches and comes in close vicinity to the capacitor. This approach has an influence on a measurable property of the capacitor, e.g. on the capacitance thereof. This modification of the capacitor is measurable as/or detectable by the processor 140.

With the illustrated examples the first information type 410 includes or is limited to generic information about a medicament to be administered by the drug delivery device 1. The first information type 410 includes a first information content 411, such as the name of the medicament or the drug. The first information content further includes an information content 412 representative of the LOT number of the drug container provided with the drug or medicament. The information content 413 is indicative of a production date. The information content 414 is indicative of a production site of the medicament. The information content 415 is indicative of a prescribed or recommended storage temperature at which the medicament should be stored during shipment and when not in use. The information content 416 is indicative of a volume of a drug or medicament container. The information content 417 is indicative of a concentration of the active ingredient of the medicament or drug. The information content 418 is indicative of a best before date or use by date of the medicament provided in the medicament container.

The numerous examples of numerous information contents 411, 412, 413, 414, 415, 416, 417, 418 are non-exclusive and show numerous examples of information contents of a first information type which is limited to generic or inherent information related to the medicament.

The information contents of the second information type, include information about a momentary status, about an actual use or about a prior use of the drug delivery device or of the respective medicament. For instance, the information content 451 is indicative of a battery level of a battery 150 of the electronic label 100. The information content 452 is indicative of an instruction to the user to remove the protective cap of the drug delivery device 1. The information content 453 includes or includes an instruction to a user to set a dose of the medicament of a particular size X. The information content 454 is indicative of an instruction to inject a dose. The information content 455 is indicative of information when the last or previous dose of the medicament has been dispensed or administered.

The further information content 456 is indicative of a point of time when administering of a next dose is due. The information content 457 of the second information type 450 is indicative of a remaining content of the medicament in the medicament or drug container. The further information content 458 is indicative that a dose administering process, e.g. a dose injection process has been completed and the further information content 459 of the second information type 450 includes an instruction to a user of the drug delivery device to wait for a number of seconds after completion of the dose before withdrawing an injection needle from an injection site.

Insofar and as illustrated in FIG. 4, the numerous information contents 411, 412, 413, 414, 415, 416, 417, 418 of the first information type 410 may represent generic or basic information with regard to the medicament. The first information type, in particular the information contents of the first information type are limited to a particular type and individual or generic properties of the medicament. The information contents 451, 452, 453, 454, 455, 456, 457, 458 and 459 of the second information type 450 are related to the use and handling of the medicament and/or of the drug delivery device. They may include information contents that are subject to dynamic changes, such as a time of a last dose or the time of setting and administering of a next dose. The information contents of the second information type might be limited to information regarding use and/or the momentary status of the medicament and/or of the drug delivery device.

In the sequence of FIGS. 5-8 numerous display configurations of the visual appearance of the electronic display 110 are illustrated at different times $t_0$-$t_3$.

Figure 5:
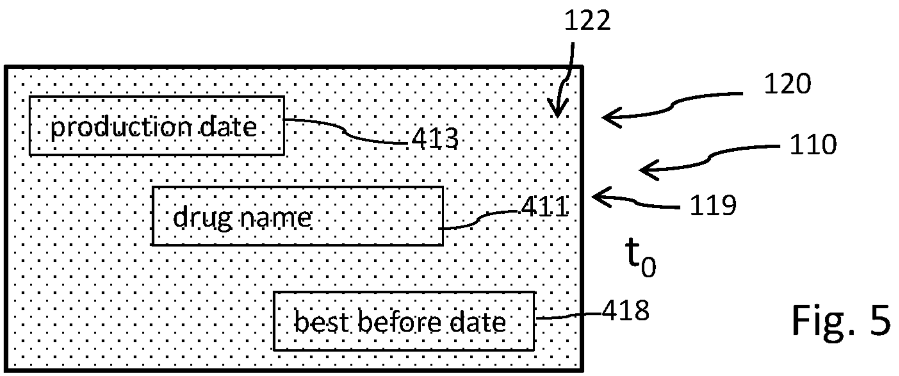
FIG. 5 is illustrative of a first display configuration at a first time.

FIG. 5 is illustrative of a first configuration of the electronic display 110 at a time $t_0$. There, numerous information contents, namely information contents 411, 413 and 418 are simultaneously provided on the electronic display 110. Here, information content 411 illustrates a drug name. Information content 413 illustrates a production date and information content 418 illustrates a best before date. The electronic display 410 may be implemented as a color display 120. It may include an information background 122 that distinguishes in color and/or brightness from the information contents 411, 413, 418. In the example of FIG. 5, the display 110 may include a LED display 119.

Figure 6:
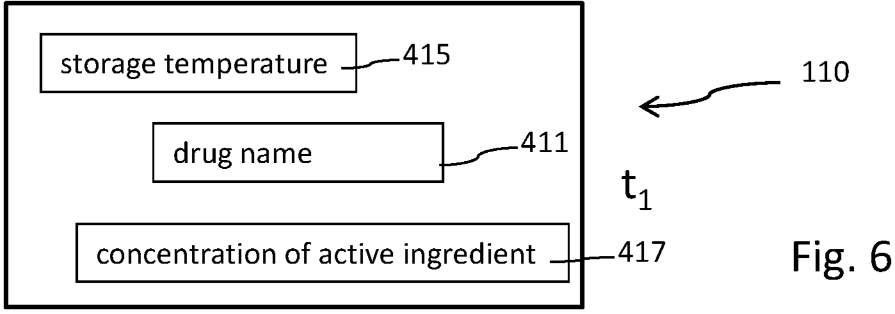
FIG. 6 is illustrative of a second display illustration at a second time.

At a time $t_1$ and as the processor 140 is configured to autonomously or to automatically switch the configuration of the electronic display 110 as illustrated in FIG. 6. While the information content 411 remains on the electronic display 110 the information contents 413, 418 as illustrated in FIG. 5 have been replaced by other information contents 415, 417. Here, information contents 413, 418 that are of the first information type 410 are replaced by other information contents 415, 417 that are also of the first information type 410. Instead of a production date 413 now a storage temperature 415 is illustrated. Instead of a best before date 418 a concentration of the active ingredient 417 is illustrated.

Figure 7:
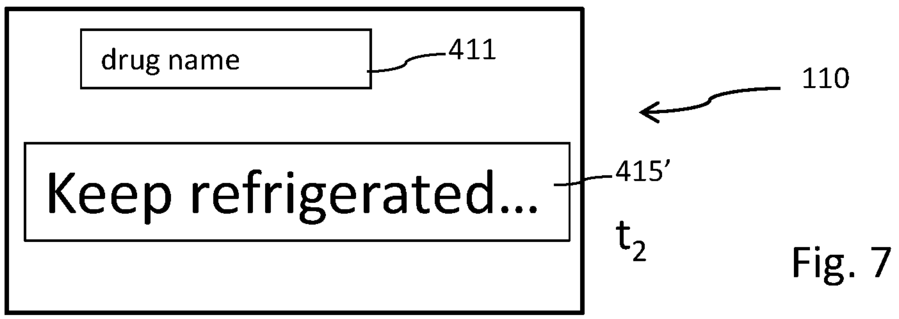
FIG. 7 shows a further display configuration at a further time.

In FIG. 7 another configuration of the electronic display 110 is illustrated. Here, the processor 140 is for example configured to automatically switch from the display configuration as illustrated in one of the FIG. 5 or 6 into the display configuration as illustrated in FIG. 7. Here, the drug name 411 is still illustrated on the electronic display 110. In addition, a first portion 415' of an information content 415 of the first information type 410 is illustrated simultaneous to the information content 411. The first portion 415' of the information content 415 is visually illustrated by comparatively large characters or symbols. For instance, the information content 415 being indicative of a recommended storage temperature may include a sequence of letters or words, such as 'keep refrigerated between 2° C.-8° C.'. In order to provide a good legibility of this rather large information content 415 the processor 140 is configured to split the information content 415 into at least two or numerous portions 415', 415''.

Figure 8:
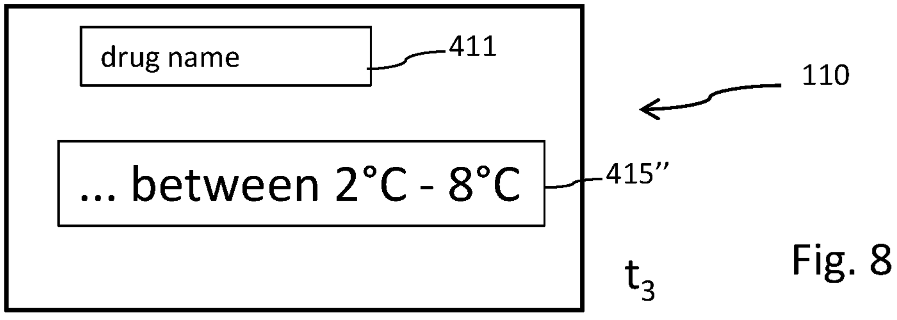
FIG. 8 shows another display configuration at a further time.

As it becomes apparent from a comparison of FIGS. 7 and 8, the processor 140 is now configured to separately, sequentially or alternately illustrate only one of a first portion 415' of the information content 415 and a second portion 415'' of the respective information content 415 at a time. Hence, at a time $t_2$ the first portion 415 of the information content 415 is illustrated on the display 110. At a later point of time a second portion 415'' of the respective information content 415 is illustrated on the electronic display 110 at a time $t_3$. Switching between the display configurations as shown in FIGS. 7 and 8 may be triggered automatically, e.g. after lapse of a predefined time interval. Moreover, the processor 140 may be configured to alternately illustrate the numerous portions 415', 415'' of the information content 415. Hence at a time $t_3$ and after lapse of a further predefined time interval the processor 140 may be configured to return to the display configuration as shown in FIG. 7.

Splitting of an information content 415 into numerous portions 415', 415'' allows to increase the size of illustration of the respective portions on the electronic display and to visualize a sequence of the respective portions. In this way, a rather extensive information content can be displayed on the electronic display 110 in a temporal sequence.

The switching between numerous display configurations may be triggered by the processor 140 in accordance to a predefined schedule. With other examples the switching between numerous display configurations may be triggered by a sensor, such as a device sensor 170 and/or an ambient sensor 190. Moreover, the electronic label 100 may be provided with a user-actuatable input 128, 129 as for instance illustrated in FIG. 24 by way of which switching between numerous predefined display configurations can be triggered by the user himself. Here, the input 128 may be implemented in a switch 154, way of which a battery 150 can be separated from the processor 140, e.g. to save battery power. With some examples, there may be provided a separate input 129 connected to the processor 144 located outside the electronic display 110. With other examples, a touch sensitive area of the display 110 may serve as an input 128.

In the sequence of FIGS. 5-8 a situation is illustrated, wherein the processor is configured to exclusively illustrate information content of the first information type 410. Generally, the processor 140 is by no way limited to show or to illustrate only one of the at least two available information types. The processor 140 may be further configured to induce visualization or illustration of information contents of the first information type and information contents of the second information type either separately, simultaneously or sequentially. This is for instance illustrated in the sequence of FIGS. 9-12. There, in FIG. 9, an example of an input 128 is also illustrated. The input 128 can be implemented as a touch-sensitive area on the electronic display. With some examples, the entirety of the electronic display 110 can be implemented as a touch-sensitive area. So simply by touching the input 128 a user may trigger switching the electronic display 110 between numerous display configurations.

Figures 9, 10, 11, 12:
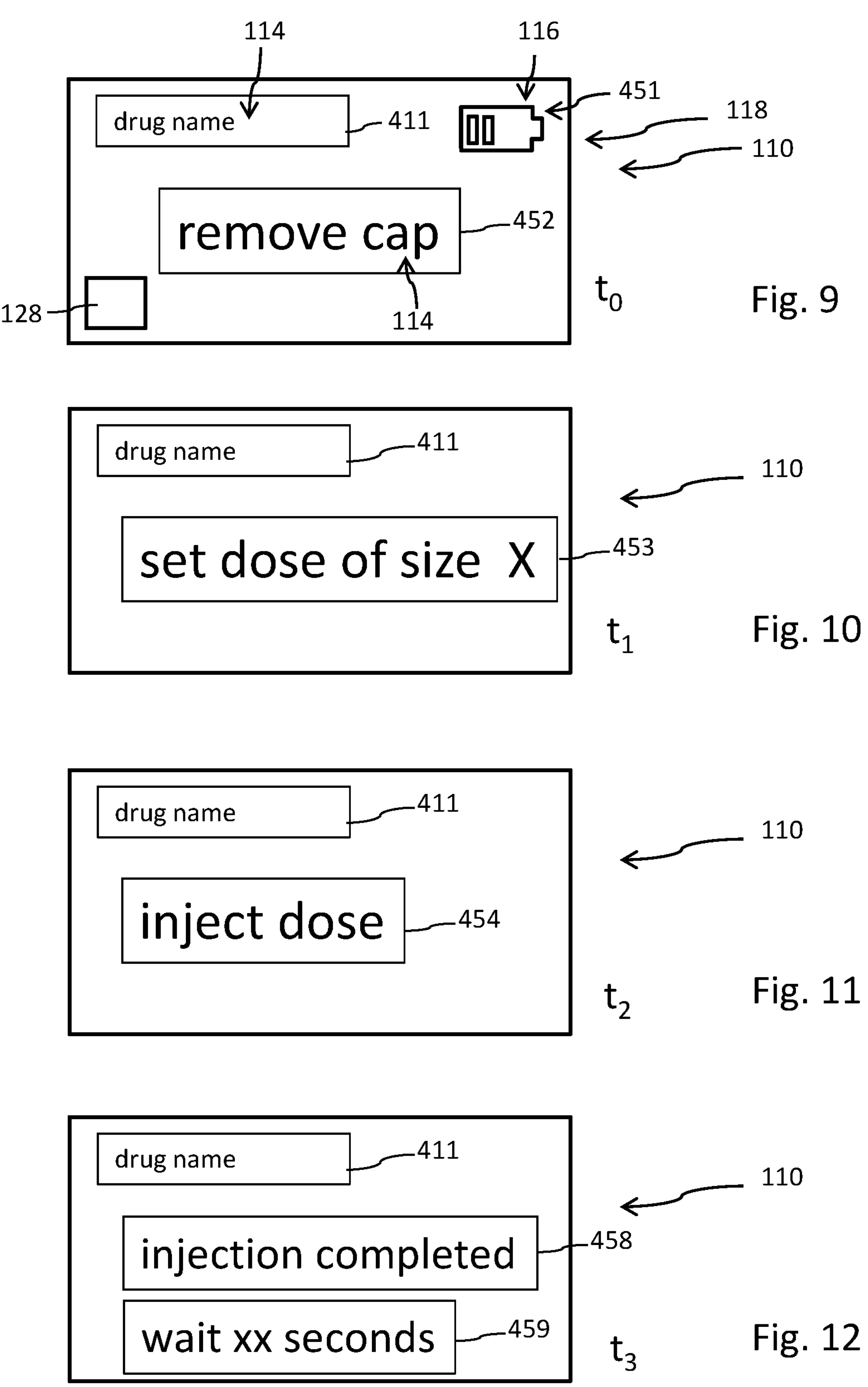
FIG. 9 is illustrative of another display configuration at a first time, wherein the display configuration provides information contents of the first and the second information type.
FIG. 10 shows a further display configuration at a further time.
FIG. 11 shows a further display configuration at a further time.
FIG. 12 shows a further display configuration at a further time.

In the sequence of FIGS. 9-12 a further example of a temporal sequence of numerous display configurations is illustrated. In FIG. 9 and at a time $t_0$ the processor 140 is controlling the display 110 in such a way, that a first information content 411 of the first information type 410 is illustrated simultaneously to a second information content 451 of the second information type 450. In addition, there is provided a further information content 452 of the second information type 450. The information content 451 is indicative of a charge level of the battery 150. The information content 451 includes a respective visual symbol 116 being indicative of the charge level of the battery 150.

The information contents 411, 452 each include a number of visual signs or characters 114, which in the case of the information content 411 are indicative of a drug name and in the case of information content 452 being indicative of a command directed to a user of the device, namely to remove a protective cap 18.

As indicated in the sequence of FIGS. 9-12, the information content 411 of the first information type 410 remains constantly on the electronic display 110 during the sequence of different display configurations at times $t_1$, $t_2$ and $t_3$.

It is only and exclusively the further information content 452 that changes to another information content 453 at the time $t_1$. At a later time $t_2$ the information content 453 of the second information type switches to another information content 454 which is also of the second information type. Thereafter, and as illustrated in FIG. 12 at time $t_3$ the information content 454 switches to a simultaneous illustration of information contents 458, 459. By way of example, the information content 453 as illustrated in FIG. 10 is indicative of a user command encouraging the user to set a dose of a particular size X. The information content 454, which is also of the second information type 450 indicates to the user, that a dose should now be injected, e.g. by depressing of a trigger 11 of the drug delivery device. Thereafter and at time $t_3$ and as illustrated in FIG. 12, the electronic display 110 simultaneously visualizes the information contents 458, 459 being indicative of the current status of the drug delivery device 1. The information content 458 is indicative that an injection procedure has been completed. The further information content 459 provides the user instruction to wait for a number of seconds before withdrawing the needle from punctured tissue.

Switching between the numerous display configurations as illustrated in FIGS. 9-12 may be either induced by a user, e.g. by actuating or depressing the input 128 each time a particular step of use of the drug delivery device 1 has been performed. Additionally or alternatively, the electronic label 100, in particular the processor 140 may be connected to at least one of a device sensor 170 and an ambient sensor 190. For instance, the device sensor 170 is configured to allocate and/or to determine a position and/or a rotational state of a dose tracker 176 of the drug delivery device 1 when the electronic label 100 is attached to the body 10 in a predefined manner.

The ambient sensor, typically integrated into the label 100 and/or arranged on the flexible substrate 101 is one of an ambient brightness sensor, and acceleration sensor, a magnetic sensor, an orientation sensor, a temperature sensor or an air pressure sensor. When implemented as an orientation sensor, acceleration sensor or ambient air pressure sensor, the ambient sensor 190 is configured to generate at least one electric signal processable by the processor 140, in particular when the electronic label 100 is subject to an acceleration, a movement or reorientation with regard to the field of gravity. By way of at least one of the device sensor 170 and the ambient sensor 190 different configurations or states of the drug delivery device 1 can be autonomously monitored and detected. In accordance to electric signals obtained from at least one of the device sensor 170 and the ambient sensor 190 the processor 140 is configured to switch between the numerous display configurations such as illustrated in the sequence of FIGS. 9-12.

Figure 13:
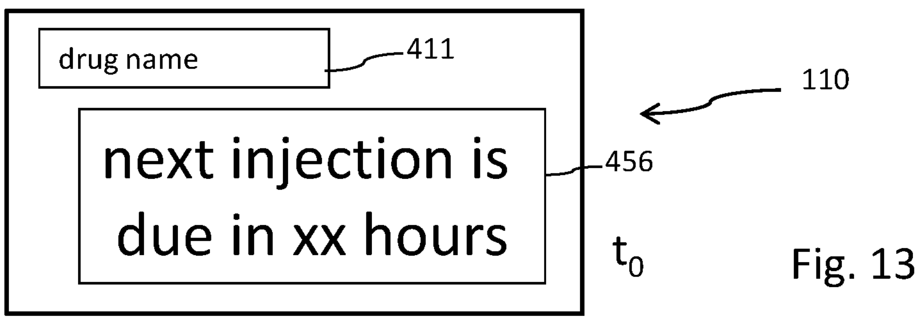
FIG. 13 shows another display configuration.
Figure 14:
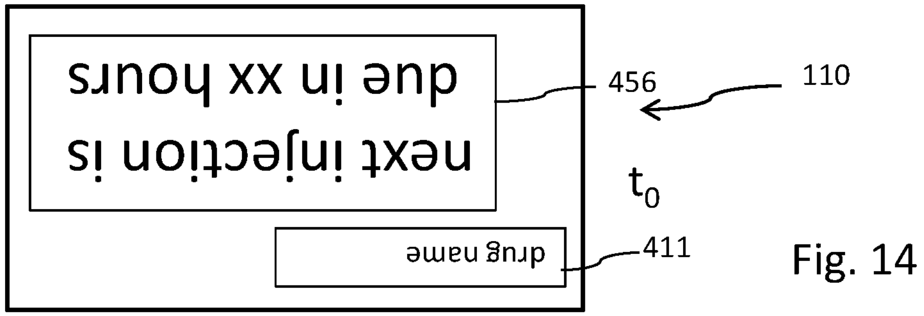
FIG. 14 shows the display configuration of FIG. 13 in an inverted or flipped orientation.

Moreover, and as illustrated by a comparison of FIGS. 13 and 14, the processor 140 is operable to turn or to flip an orientation of at least one of the information contents 411, 456 that may be of the same or of different information types 410, 450. Typically, the processor 140 is configured to flip or to reorient the entire visual appearance of the display 110 on the basis of an electric signal received from the ambient sensor 190. For this, the ambient sensor 190 may be implemented as an acceleration sensor or orientation sensor. The momentary orientation of the first information content 111 and/or of a further information content 456 will be flipped by 90°, by 180° or by 270°. For instance, it may be oriented upside down when the respective signals from the ambient sensor 190 are indicative of a respective turning of the electronic label 100 with respect to the gravitational field.

The orientation of numerous information contents 411, 456 on the display 110 may strictly follow a momentary orientation of the label 100 in the gravitational field. With some examples, the variable orientation of the numerous information contents 411, 456 may align parallel to the lateral borders of the electronic display 110, which may be rectangular.

Figure 15:
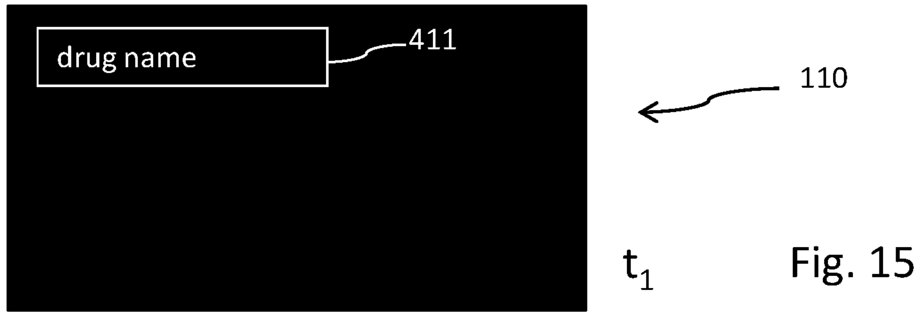
FIG. 15 is illustrative of a display configuration when the display is in an idle or in a power saving mode.

In FIG. 15 an idle mode or a power saving mode of the electronic display 110 is illustrated. Compared to, e.g. a configuration of the electronic display 110 as illustrated in one of the FIGS. 5-14, the brightness of the electronic display 110 is reduced and the information content 411 illustrated on the display is reduced to a minimum. It may be reduced to an illustration of a drug name.

Figure 17:
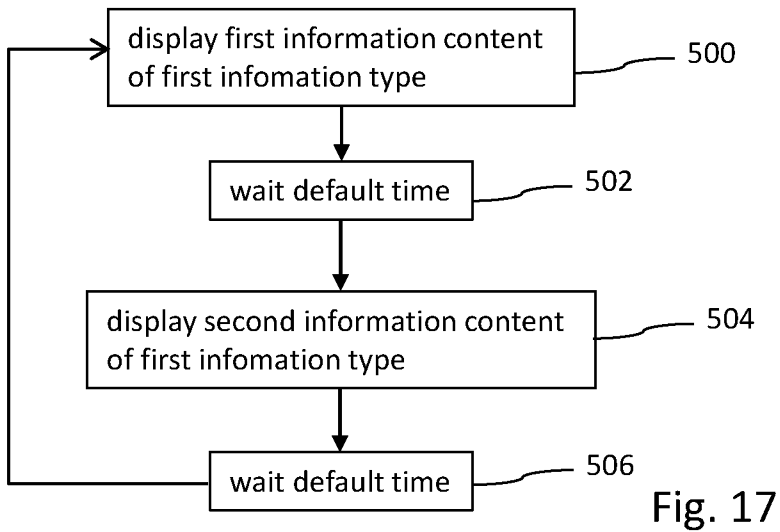
FIG. 17 is illustrative of a flowchart of an example of the method of visualizing first and second information contents on the electronic display.

In FIG. 17 one example of a method of visualizing a first information content of a first information type 510 and a second information content of a second information type 450 on an electronic display 110 of an electronic label 100 is illustrated. Here, in a first step 500 a first information content, e.g. a drug or medicament name 411, which is an information content of the first information type 410 is illustrated on the display. The processor 140 is then configured to wait for a predetermined or default time in step 502. For this, the processor 141 is equipped with a clock generator 141. In a further step 504 and after lapse of the predetermined or default time interval the processor 140 switches into a further display configuration rather autonomously. Hence, in step 504 and with the further display configuration a second information content of the first information type is illustrated on the display 110. Thereafter, the processor 140 waits again for a default or predetermined time interval in step 506. Thereafter, the method may return to step 500 and the display 110 may return into an initial display configuration.

In step 504 and instead of displaying a second information content of first information type the processor 140 may also illustrate a third information content which is of the second information type. The second information content or third information content as displayed in step 504 may be displayed in addition to the first information content already present in step 500. With some examples, the second information content and/or the third information content in step 504 replaces the first information content on the electronic display 110.

Figure 18:
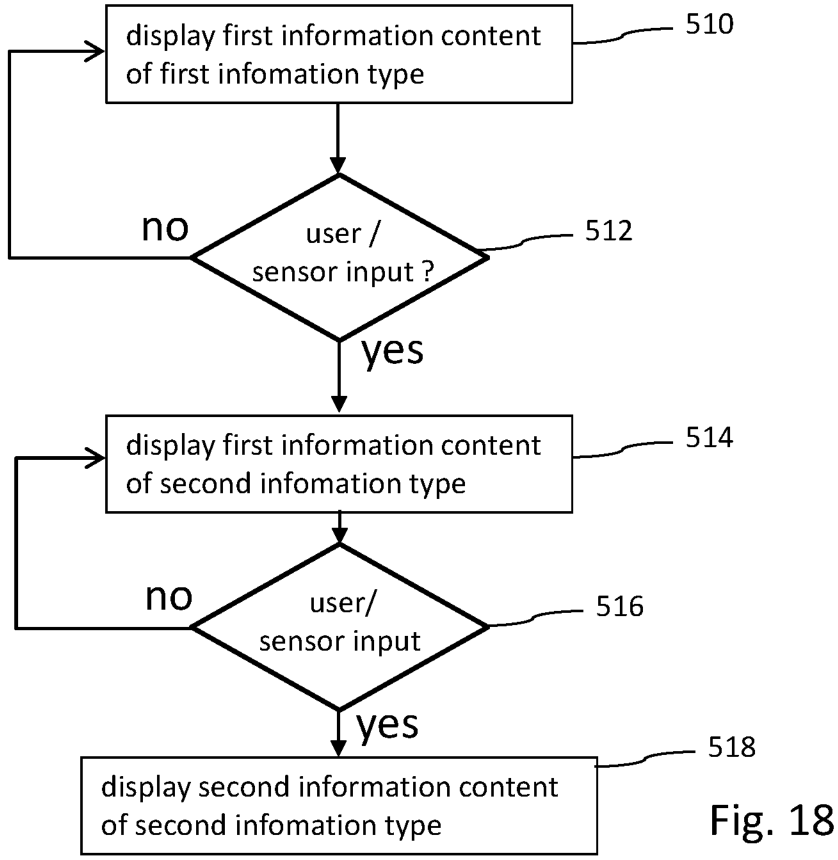
FIG. 18 is illustrative of a further flowchart of the method.

A further example of the method is shown in FIG. 18. Here, and in a first step 510 the processor 140 is configured to display a first information content of the first information type. The method proceeds then with step 512. Here, the processor 140 is monitoring or waits for a user input or sensor input. As soon as a user input or sensor input is detected the method proceeds with step 514, in which a first information content of second information type is illustrated on the display 110. In case there is no user input or sensor input in step 512 the method returns to step 510. In this way the first information content as displayed in step 510 remains on the electronic display 110 until a user input or sensor input is detected.

Instead of displaying a first information content 451 of second information type 450 there may be provided another information content of the first information type simultaneously or instead of providing an information content 451 of the second information type 450. Then and as the method proceeds with step 516, the processor 140 again waits for an input of a user or a signal from at least one of the ambient sensor 190 and the device sensor 170. As soon as a user input or a sensor input is detected in step 516, the method proceeds with step 518, thereby switching the display configuration so as to display a second information content of the second information type 450. Instead or in addition there may be also illustrated a second information content of first information type in step 518. As long as no input from a user or from a sensor is detected in step 516 the method returns to step 514.

In the absence of a user input or sensor input the loop of the steps 514, 516 may be interrupted by the processor 140 after lapse of a further predefined time interval. For this, the processor 140 may be configured to start a counter as the method jumps from step 512 to step 514. In the absence of user input or sensor input and when the timer reaches a predefined maximum time in step 516 the processor 140 may be configured to switch from step 516 back to step 510. In this way the display configuration of step 514 may only persist temporally and during a maximum time interval as defined by the timer or counter of the processor 140. If there is no user input or sensor input in step 516 over a predefined time interval the method returns to step 510, in which a default display configuration is illustrated.

Figure 19:
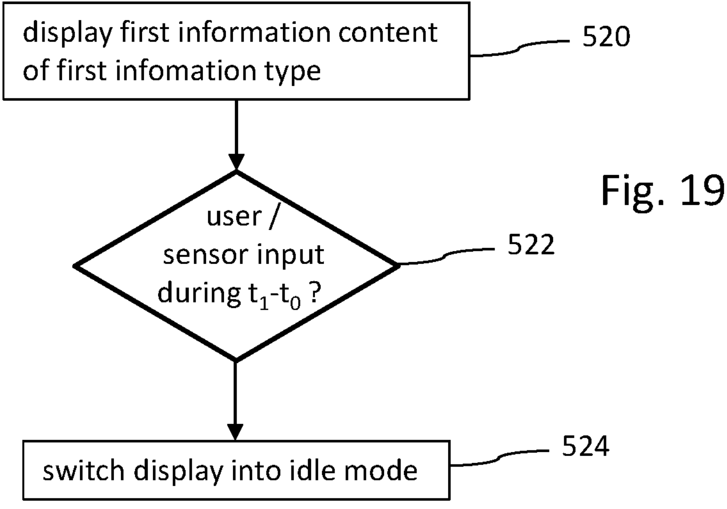
FIG. 19 represents a flowchart illustrating a further example of the method and FIG. 20 is illustrative of a further example of the method of visualizing first and second information contents on the electronic display.

In FIG. 19 a further flowchart illustrating the working principle of the electronic label 100 is illustrated. There, in a first display configuration in step 520 a first information content of first information type is illustrated, such as the medicament name 511. In a subsequent step 522 the processor 140 monitors an input of a user or an input of a sensor during a predefined time interval. If there is no user input during the predefined time interval the method proceeds with step 524, and switches the display into the idle mode.

With another example quite similar to the flowchart of FIG. 19, the display may be switched into a power saving mode in step 524 if in the preceding step 522 the processor 140 detects a battery level that is below a predefined minimum allowable battery level. In still another example and when in step 522 the processor 140 detects or identifies an alert situation it may activate a warning buzzer 146 in step 524.

Figure 20:
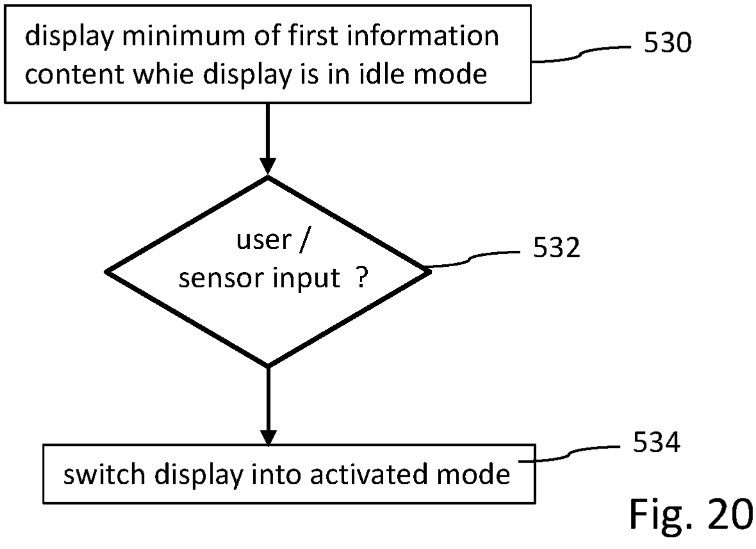

In the further flowchart of FIG. 20 a situation is illustrated, wherein in step 530 the electronic display 110 is in an idle or power saving mode. Here, the display 110 only provides a minimum of a first information content, e.g. a medicament name or other information contents of the first information type in order to fulfill regulatory requirements of the electronic label. In step 532 there is detected an input of a user and/or a signal of one of the sensors 170, 190. This is treated as a wake up signal and the processor 140 is then configured to switch the display into an activated mode in step 534.

The different types of information 410, 450 may be stored separately in a storage 144 of the processor 140 or of an electronic circuit 130 as illustrated in FIG. 24. For this, the storage 144 may include memory blocks 145 of read only memory type (ROM) and memory blocks 147 of erasable programmable read-only memory type (EPROM). With some examples the information contents of the first information type are stored in ROM memory blocks 145. With some examples the information content of the second information type is stored in EPROM memory blocks 147. Insofar, the information content of the first information type 410 may be stored in the data storage (ROM) in a non-modifiable format. The information content of the second information type 450 may be dynamically modified or overwritten by the processor 140.

The example of an electronic circuit 130 of FIG. 24 is by no way limiting for the examples of FIGS. 3-26. The electronic display 110 may superimpose the electronic circuit 130. Hence, the electronic display 110 may entirely overlap with the electronic circuit 130 located underneath. The electronic display 110 may include a multilayer structure as indicated in FIGS. 22 and 23.

The electronic circuit 130 may be implemented in one or several of the various layers 103, 104, 105, 106 of the flexible label 100. Typically, the electronic circuit 130 is entirely provided by a conductive layer 103.

The input 128 or touch sensitive area may be visually indicated on the electronic display 110 112 or on a separate portion outside the electronic display 110. The input 128 and the electronic display 110 are configured to interact in such a way, that upon touching or depressing of the input 128, i.e. the touch sensitive area at least the second electronic display 110 changes its visual appearance. The electronic display 110 may be switchable between a default mode or idle mode and an activated mode.

In a further example and upon touching depressing of input 128 the processor 140 may be configured to record a user activity and/or a point of time of a user activity in the electronic storage 144 or memory of the electronic circuit. The electronic storage 144 may include capacity to store data relating to a plurality of events including time stamps.

In a further example the electronic circuit includes an antenna 160 providing a data transmission element, e.g. enabling NFC, WIFI or RF data transmission. This way data stored in the memory can be read out by an external device using a respective wireless communication protocol. NFC or RF communication could be implemented in passive or active way, wherein the latter requires an energy source, e.g. battery, powering the electronics. The battery may be implemented in printing technology.

FIG. 24 shows one example of an electronic circuit 130 of the electronic label 100. The electronic circuit 130 may be directly printed on the flexible substrate 101. The electronic structures and/or the conductive structures of the electronic circuit 130 might be bendable or flexible as well. The integrity or functionality of the electronic circuit 130 is substantially unaffected by a bending or flexing of the flexible substrate 101 and/or of the electronic circuit 130.

The electronic circuit 130 includes a battery 150 typically equipped with numerous battery cells 152. The individual battery cells 152 are electrically connected. They may be connected in series or parallel depending on the voltage provided by the individual battery cells 152 and depending on the voltage required by the processor 140. The battery 150 and/or its battery cells 152 may include a printed electronic structure. Hence, the battery 150 and/or the battery cells 152 our printed batteries or battery cells and may be arranged on the substrate 101 by way of printing.

The processor 140 is connected to the battery 150 as well as to the electronic display 110. The interconnection between the battery 150 and the processor 140 may be interrupted by the switch 154 coinciding with the input 128. Depressing of the switch 154 may either connect or disconnect the electrical connection between the battery 150 and the processor 140.

The processor 140 includes a central processing unit (CPU) 142 and the storage 144. In the storage 144 numerous predefined information contents 411, 412, 413, 451, 452, 453 for illustration with the electronic display 110 may be stored. Upon registration of a closing or opening of the switch 154 a predefined information content 411 such as a medicament name might be illustrated or displayed on the electronic display 110. When equipped with a data storage 144 the processor 140 may be further configured to count a number of touch operations of the input 128. If the processor 140 is further equipped with a clock generator 141 every input or touch instant can be further assigned with a timestamp thus allowing to record a dosing history or to record the points in time at which the input 128 was appropriately touched by the user of the injection device 1.

The antenna 160 is typically connected to the processor 140 and is configured for wireless data transmission. The antenna 160 may be configured as a receiving antenna and/or as a broadcasting antenna. The antenna 160 may be configured to transmit electromagnetic signals in the RF frequency band. The antenna 160 may include an RFID antenna. The antenna 160 may be configured in accordance to conventional wireless communication standards, such as Bluetooth, NFC or IEEE 802.11 (WIFI). The antenna 160 is configured to exchange data with an external electronic device 300, such as a smart watch, a smartphone, a tablet computer or a personal computer.

The processor 140 may be reconfigurable by signals obtained from the external electronic device 300 via the antenna 160. In this way the external electronic device 300 can be used to modify or to reconfigure the processor 140 and hence to modify and to reconfigure the content of electronic display 110. In addition or alternative the external electronic device 300 may be further configured to read out the data storage 144 of the electronic circuit 130. In this way the dosing history and the use of the label 100 can be precisely monitored and transmitted to the external electronic device 300 for further processing and/or evaluation.

The entirety of the electronic components of the electronic circuit 130, e.g. the wired connections between the battery 150 and the battery cells 152, the switch 154 or the touch sensitive area forming the input 128, the antenna 160 as well as the processor 140 may include or may be formed by a printing process on the substrate 101. In this way a separate assembly and arrangement of numerous electronic components on the substrate 101 becomes substantially superfluous. This enables a cost-efficient mass manufacturing of the label 100.

A lower side of the substrate 101 may be provided with an adhesive. The adhesive may be provided on an adhesive layer 102 entirely or at least partially covering the lower side of the substrate 101 located opposite to the conductive layer 103 on which the electronic circuit 130 is located. In FIG. 23 a stack of numerous layers 103, 104, 105, 106 configured to form the electronic display 110 is exemplary illustrated. The stack structure of FIG. 23 may represents a thin film electroluminescent electronic display. The substrate 101 may be pliable and may include or consist of one of the following: foldable office paper, transparent or non-transparent PET film, leather, wood, ceramics, and a metal foil. The electroluminescent display is configured to actively emit light.

A segment of the display consists of two overlaid electrodes that act as a capacitor. The oppositely located electrodes are provided in the conductive layer 103 and in the transparent electrode layer 106. Between these layers 103, 106 there is provided a dielectric layer 104 and an electroluminescent layer 105, e.g. in form of a phosphor layer. If a suitable voltage and a suitable current AC signal is applied the electroluminescent layer 105 emits photons.

The stack of layers 103, 104, 105, 106 may add only 100-150 μm of thickness to the substrate 101. In this way the electronic display 110 can be extraordinarily thin.

With other examples the flexible electronic display 110 is implemented as an electrophoretic display that is based on rearranging charged pigment particles by means of an applied electric field. There, titanium dioxide particles of appropriately 1 μm in diameter may be dispersed in a hydrocarbon oil. A dark colored dye is added to the oil along with surfactants and charging agents that cause the particles to take on an electric charge. This mixture is placed between two parallel, conductive plates separated by a gap of 10-100 μm. When a voltage is applied across the two plates the particles migrate electrophoretically to the plate that bears the opposite charge from that on the particles.

When the particles are located at the front or a viewing side of the display, it appears white because light is scattered back to the viewer by the high index titania particles. When the particles are located at the rear side of the display it appears dark because the incident light is absorbed by the colored dye. If the rear electrode is divided into a number of small picture elements or pixels, an image can be formed by applying the appropriate voltage to each region of the display to create a pattern of reflecting and absorbing regions. Electrophoretic displays are considered prime examples of an electronic paper category because of their paper-like appearance and lower power consumption.

The label 100 may only be optionally equipped with an antenna 160. With one implementation the label 100 may be void of an antenna 160 and may be operable to illustrate a well-defined or predefined information content 411, 451 and to provide a switching between a sleep mode or activated mode.

Figure 25:
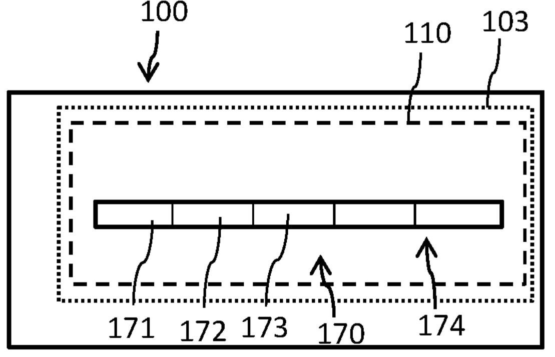
FIG. 25 shows another example of the electronic label equipped with a sensor.
Figure 26:
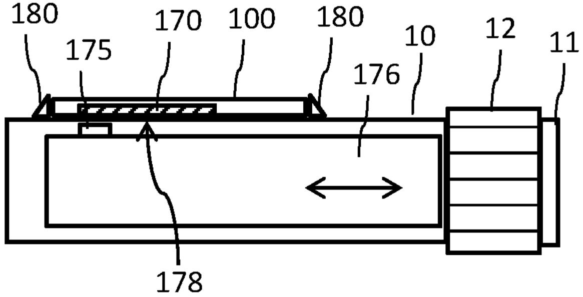
FIG. 26 shows a cross-section through the injection device with the electronic label attached thereto.

In FIGS. 25 and 26 there is illustrated a further example of a flexible label 100. This label 100 may be implemented with or without an antenna 160. It includes a flexible substrate 101 with an electronic display 110. Typically, the label 100 of FIG. 25 also includes a processor 140, a CPU 142, a data storage 144 and a battery 150 as described above in connection with FIG. 24. In addition, the label 100 of FIGS. 25 and 26 includes a device sensor 170.

The device sensor 170 is configured to allocate or to determine a position and/or a rotational state of a dose tracker 176 of the injection device 1 when the label 100 is attached to the housing 10 in a predefined manner. Here, the dose tracker 176 may coincide or may represent the dose tracker 50 as described above in connection with FIGS. 1-2. Alternatively, the dose tracker 176 may be represented by any other component of the injection device 1. The dose tracker 176 may be represented e.g. by the piston rod 20 or by some arbitrary component of the drive mechanism 8 or dose setting mechanism 9, wherein the position and/or orientation of the respective device component relative to the housing 10 is indicative of a size of a dose currently set or dispensed.

For arranging the label 100 to the housing 10 the housing 10 may include at least one or several position marks 180 illustrated in FIG. 26 as protrusions on the outside surface of the housing 10. The label 100 has to be properly attached to the housing 10 in the area as defined by the at least one or several position marks 180. The dose tracker 176 may coincide with the number sleeve 80 of the injection device 1 or may be formed by the number sleeve. The dose tracker 176 includes an indicator 175 whose positional state, i.e. the longitudinal position and/or a rotational orientation relative to the housing 10 is detectable by the device sensor 170.

The position mark 180 may protrude from the sidewall of the housing 10 or may include a recess in the housing 10. Alternative, the position mark 180 may be void of protrusions or recesses in the outside surface of the housing 10. The position mark 180 may simply include a visual indication, such as a border region inside which the label 100 should be fastened, e.g. adhesively attached.

In one example the device sensor 170 includes numerous discrete sensor segments 171, 172, 173 that are separated along a moving direction of the indicator 175 and/or of the dose tracker 176 relative to the housing 10. As the dose tracker 176 is subject to a rotational and/or sliding movement relative to the housing 10 the indicator 175, e.g.

initially overlapping with a first sensor segment 171 moves towards a second sensor segment 172 and, e.g. further towards the third sensor segment 173. The movement of the indicator 175 relative to the numerous sensor segments 171, 172, 173 is detectable by the device sensor 170 that is electrically connected to the processor 140. In this way, the processor 140 and the device sensor 170 are configured to determine and to detect an actual position and/or rotational state of the indicator 175 and hence of the dose tracker 176 relative to the housing 10.

The position or rotational state of the dose tracker 176 unequivocally coincides with a size of a dose actually set by the injection device 1. In this way, the processor 140 may be configured to determine or to measure a size of a dose actually set with the injection device 1 when the label 100 is appropriately connected to the housing 10. The determined longitudinal or rotational position of the dose tracker 176 may be thus compared with a predefined position, e.g. indicated by the second information content 111 on the electronic display 112. The dose actually set with the injection device may be further illustrated through the dosage window 13.

The specific implementation of the device sensor 170 and the indicator 175 may vary. As illustrated in FIG. 26 the housing 10 may include a through opening 178 or a recess through which the position of the indicator 175 can be for instance mechanically or electrically detected, e.g. by means of numerous contact pins provided on each sensor segment 171, 172, 173. For this, there may be established a direct mechanical contact between the indicator 175 and at least one of the sensor segments 171, 172, 173.

With other examples the indicator 175 may be magnetically encoded and the sensor segments 171, 172, 173 may be configured to detect a magnetic field of the indicator 175 as the indicator 175 is subject to a longitudinal and/or rotational movement. With a further example the indicator 175 and the sensor segments 171, 172, 173 may be implemented electrostatically. Here, the numerous sensor segments 171, 172, 173 may be configured to allocate or to detect a modification of an electric field induced by the indicator 175. Furthermore, the sensor segments 171, 172, 173 may include capacity measuring elements configured to measure a modification of an electric field or electric capacitance in the vicinity of the respective sensor segments 171, 172, 173. Magnetic, electrostatic and capacitive measurement procedures may be of particular benefit because they may not require a through opening 178 or recess in the sidewall of the housing 10. With such implementations the label 100 may be simply adhesively attached within the given position marks on the outside surface of the body 10.

With the example as illustrated in FIGS. 22 and 23 there may be provided at least one electrode structure 174 of a device sensor 170 on the flexible substrate 101. At least one or all of the sensor segments 171, 172, 173 as described above may belong to or may constitute the electrode structure 174. The electrode structure 174 may be located between the adhesive layer 102 and at least one of the conductive layers 103, 106. The electrode structure 174 may belong to the device sensor 170 or it may be part of the device sensor 170. The electrode structure 174 on the substrate 101 is configured to measure at least one of an electric capacitance, an electric field and a magnetic field in the vicinity of the substrate 101. Typically, the electrode structure 174 is configured to determine or to quantitatively measure a position and/or a rotational state of at least one device component, e.g. of a dose tracker 176 of the injection device 1.

With further examples the electrode structure 174 may be configured to determine a longitudinal position of the piston rod 20 and/or the longitudinal position of the bung 7 or piston of the cartridge 6 with regards to a barrel of the cartridge 6 and/or with regards to the housing or body 10 of the injection device 1.

At least one or both of the conductive layer 103 and the transparent electrode layer 106 include(s) an electrically conductive grid electrode at least partially spatially overlapping with the electrode structure 174 of the device sensor 170. Here, and due to the spatial overlap of the conductive grid electrode 103, 106 with the electrode structure 174 of the device sensor 170 the electrically conductive grid electrode 103, 106 provides an electromagnetic shield 107 for the device sensor 170. In this way, the electromagnetic compatibility (EMC) of the label 100 can be increased and the position or orientation of the at least one dose tracker 176 can be measured and defined with high precision.

As illustrated in FIG. 25, the electrically conductive grid electrode 103 spatially overlaps with the electrode structure 174 and the numerous sensor segments 171, 172, 173 of the device sensor 170.

Figure 16:
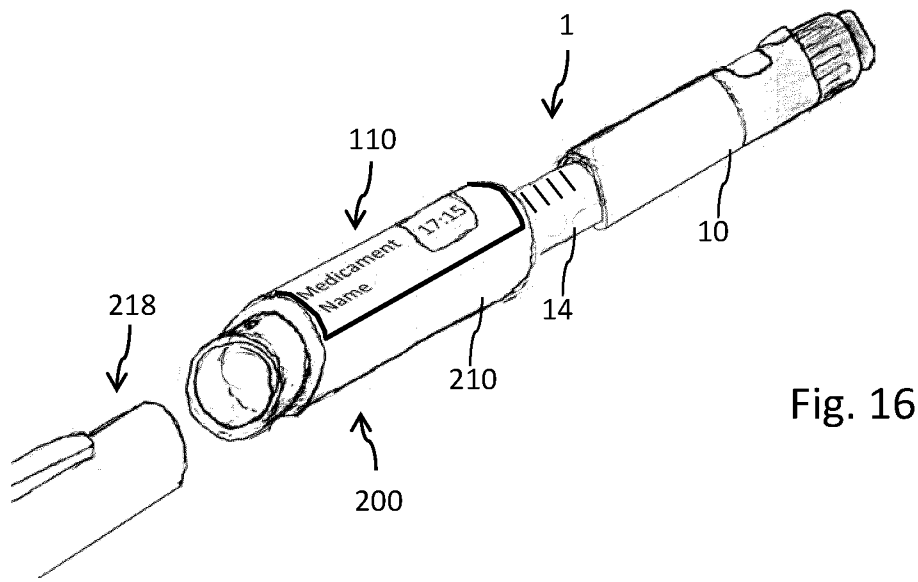
FIG. 16 is a perspective illustration of a drug delivery device provided with an adapter carrying the label, wherein the adapter is in a pre-assembly configuration.
Figure 21:
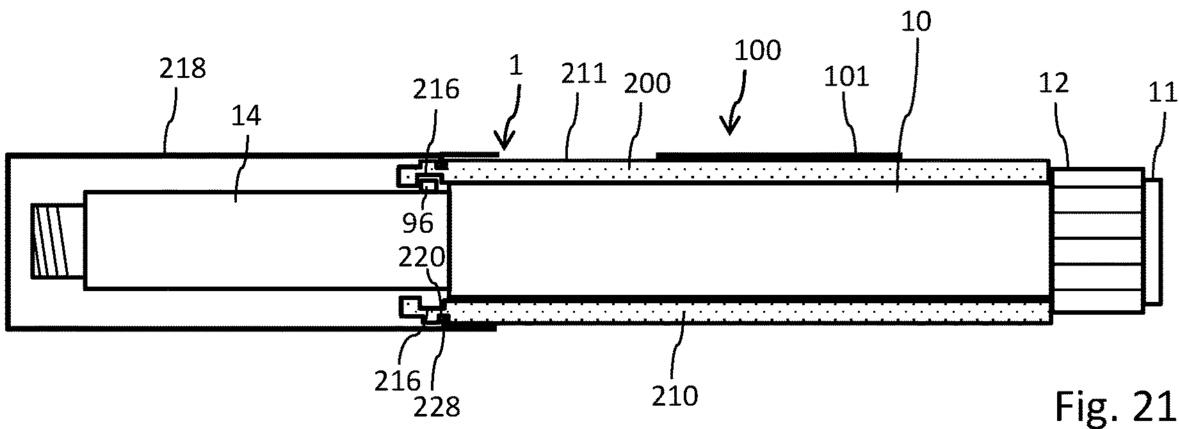
FIG. 21 is illustrative of a longitudinal cross-section through the assembly of the injection device with the adapter.

In FIGS. 16 and 21 an adapter 200 configured for a releasable attachment to the housing or body 10 of the injection device 1 is illustrated. The adapter 200 includes a rigid body 210. The rigid body 210 includes a tubular-shaped hollow sleeve sized to receive at least a distal portion of the body 10 of the injection device 1. In particular, the inner diameter of the body 210 is sized to receive the cartridge holder 14 of the injection device 1. The rigid body 210 and hence the sleeve may be also sized to receive the proximal housing or body 10 of the injection device 1 as illustrated in FIG. 21. In a final assembly configuration as illustrated in FIG. 21, a proximal end of the rigid body 210 may be located adjacent or may adjoin a distal end of the dose dial 12.

The adapter 200 and its body 210 includes at least one counter fastening feature 216 to engage with a fastening feature 96 of the housing 10 of the injection device 1. As illustrated in FIG. 21, the fastening feature 96 may include a radially outwardly extending protrusion. The protrusion may include at least one of a pin and a radially outwardly extending rim, e.g. on a proximal end of the cartridge holder 14. Typically, the fastening feature 96 is configured to engage with a respective counter fastening feature of the protective cap 18 as illustrated in FIGS. 1 and 2.

Now and for fastening the adapter 200 to the housing 10 of the injection device the adapter 210 includes the counter fastening feature 216 on an inside of its hollow sleeve. The counter fastening feature 216 is typically arranged at or near the distal end of the rigid body 210. The counter fastening feature 216 may include a recess or a groove on the inside surface of the elongated sleeve of the rigid body 210. In this way the counter fastening feature 216 and the fastening feature 96 may engage by way of a snap fit engagement. They may engage frictionally or by way of a form fit. In this way, the body 210 of the adapter 200 can be fastened in a well-defined and precise manner on the outside of the housing 10 of the injection device 1.

The body 210 includes an outside surface 211 on which the label 100 as described above is rigidly or detachably fastened. Typically, the label 100 is adhesively attached to the outside surface 211.

Since the adapter 200 is engageable with the fastening feature 96 of the injection device 1, which is originally intended for fastening of the protective cap 18 as illustrated in FIGS. 1 and 2, the protective cap 18 is replaceable and/or is actually replaced or substituted by a replacement protective cap 218. The replacement protective cap 218 is slightly larger in size at least in the region where it overlaps with the fastening feature 96 of the housing or body 10. The body 210 of the adapter 200 includes a cap fastener 220 configured and operable to engage with a counter cap fastener 228 provided on the replacement protective cap 218.

At least one of the cap fastener 220 and the counter cap fastener 228 includes a radial protrusion complementary shaped to a respective radial recess of the other one of the cap fastener 220 and the counter cap fastener 228. In this way, the replacement protective cap 218 can be mounted and fastened to a distal portion or distal end of the adapter 200 when the adapter 200 occupies the original fastening feature 96 of the housing 10 of the injection device 1.

REFERENCE NUMBERS

1 injection device
2 distal direction
3 proximal direction
4 dose incrementing direction
5 dose decrementing direction
6 cartridge
7 bung
8 drive mechanism
9 dose setting mechanism
10 housing
11 trigger
12 dose dial
13 dosage window
14 cartridge holder
15 injection needle
16 inner needle cap
17 outer needle cap
18 protective cap
19 protrusion
20 piston rod
21 bearing
22 first thread
23 pressure foot
24 second thread
25 barrel
26 seal
28 threaded socket
30 drive sleeve
31 threaded section
32 flange
33 flange
35 last dose limiter
36 shoulder
40 spring
41 recess
50 dose tracker
51 tracking stop feature
60 clutch
62 insert piece
64 stem
80 number sleeve
81 groove
90 ratchet mechanism
91 ratchet feature
95 preselector
96 fastening feature
100 label
101 substrate
102 adhesive layer
103 conductive layer
104 dielectric layer
105 electroluminescent layer
106 transparent electrode layer
107 electromagnetic shield
110 electronic display
114 visual sign
116 visual symbol
118 electrophoretic display
119 light emitting diode display
120 color display
122 information background
128 input
129 input
130 electronic circuit
140 processor
141 clock generator
142 CPU
144 storage
146 warning buzzer
150 battery
152 battery cell
154 switch
160 antenna
170 device sensor
171 sensor segment
172 sensor segment
173 sensor segment
174 electrode structure
175 indicator
176 dose tracker
178 through opening
180 position mark
190 ambient sensor
200 adapter
210 body
211 outside surface
216 counter fastening feature
218 protective cap
220 cap fastener
228 counter cap fastener
300 electronic device
410 information type
411 information content
412 information content
413 information content
414 information content
415 information content
416 information content
417 information content
418 information content
450 information type
451 information content
452 information content
453 information content
454 information content
455 information content
456 information content
457 information content
458 information content
459 information content

The invention claimed is:

1. An electronic label for a drug delivery device configured for administering of a medicament to a patient, the electronic label comprising:

a flexible substrate configured for attachment to a body of the drug delivery device;

an electronic display located on the flexible substrate, wherein the electronic display is configured to display at least a first information content of a first information type, to display at least a second information content of a second information type and to display at least a third information content, wherein the third information content is of the first information type or of the second information type, wherein the first information type comprises generic information about the medicament and wherein the second information type comprises information about a momentary status, about an actual use or about a prior use of the drug delivery device;

a processor connected to the electronic display and configured to modify or to control a visual appearance of the electronic display by displaying at least a portion of the first information content and at least a portion of the third information content separately, simultaneously, sequentially or alternately on the electronic display; and at least one ambient sensor located on the flexible substrate and connected to the processor, wherein the ambient sensor is configured to determine at least one of an ambient brightness, a variation of ambient air pressure, or to detect an orientation of the electronic label with regard to a field of gravity, wherein the processor is configured to modify at least a portion of one of the first information content and the second information content on the electronic display when receiving a sensor signal from the ambient sensor.

2. The electronic label of claim 1, wherein the processor is configured to visualize at least a portion of the second information content and at least a portion of the third information content separately, simultaneously, sequentially or alternately on the electronic display.

3. The electronic label of claim 1, further comprising a data storage connected to the processor or integrated into the processor, wherein the data storage is configured to store first information contents of the first information type and to store second information contents of the second information type.

4. The electronic label of claim 1, further comprising a clock generator connected to or integrated in the processor, wherein the processor is configured to visualize at least a portion of one of the first information content and the second information content during a predefined time interval and to visualize at least a portion of the third information content after lapse of the predefined time interval.

5. The electronic label of claim 1, wherein the processor is configured to switch the electronic display between an idle mode and an activated mode, wherein when in the idle mode the electronic display consumes less electric energy compared to when in the activated mode.

6. The electronic label according to claim 1, wherein the processor is operable to turn or to flip an orientation of at least one of the first information content and the second information content depending on an electric signal received from the ambient sensor.

7. The electronic label of claim 1, further comprising at least one input connected to the processor and actuatable by a user of the drug delivery device, wherein the processor is configured to modify the visual appearance of the electronic display upon actuation of the at least one input.

8. The electronic label of claim 1, further comprising a battery connectable to the processor, wherein the processor is configured to determine or to measure a charging level of the battery and wherein the processor is operable to switch the electronic display into a power saving mode when the charging level of the battery drops below a predefined minimum.

9. The electronic label of claim 1, further comprising a planar shaped warning buzzer connected to the processor, wherein the warning buzzer is configured to generate an audible sound when activated by the processor.

10. The electronic label of claim 1, wherein the electronic display is one of an electroluminescent display, an electrophoretic display, a liquid crystal display and a light emitting diode display.

11. The electronic label of claim 1, wherein the first information type includes at least one of the following information:

a drug name,
a LOT number,
a production date,
a production site,
a suitable storage temperature,
a volume of a drug container,
a concentration of an active ingredient, and
a best before date of the drug.

12. The electronic label of claim 1, wherein the processor is arranged on the flexible substrate.

13. A drug delivery device for administering a medicament to a patient, the drug delivery device comprising:

a housing comprising or forming a body and configured to accommodate a medicament container;

a drive mechanism configured to withdraw or to expel a dose of the medicament from the medicament container and configured to administer the dose of the medicament to a patient;

an electronic label attached to the body, the electronic label comprising:

a flexible substrate configured for attachment to the body;

an electronic display located on the flexible substrate, wherein the electronic display is configured to display at least a first information content of a first information type, to display at least a second information content of a second information type and to display at least a third information content, wherein the third information content is of the first information type or of the second information type, wherein the first information type comprises generic information about the medicament and wherein the second information type comprises information about a momentary status, about an actual use or about a prior use of the drug delivery device;

a processor connected to the electronic display and configured to modify or to control a visual appearance of the electronic display by displaying at least a portion of the first information content and at least a portion of the third information content separately, simultaneously, sequentially or alternately on the electronic display; and at least one ambient sensor located on the flexible substrate and connected to the processor, wherein the ambient sensor is configured to determine at least one of an ambient brightness, a variation of ambient air pressure, or to detect a movement and/or an orientation of the electronic label with regard to a field of gravity, wherein the processor is configured to modify at least a portion of one of the first information content and the second information content on the electronic display when receiving a sensor signal from the ambient sensor.

14. The drug delivery device of claim 13, wherein the processor is configured to visualize at least a portion of the second information content and at least a portion of the third information content separately, simultaneously, sequentially or alternately on the electronic display.

15. The drug delivery device of claim 13, further comprising a data storage connected to the processor or integrated into the processor, wherein the data storage is configured to store first information contents of the first information type and to store second information contents of the second information type.

16. A method for displaying a first information content of a first information type and a second information content of a second information type on an electronic display of an electronic label comprising: a flexible substrate configured for attachment to a body of a drug delivery device, an electronic display located on the flexible substrate, wherein the electronic display is configured to display at least a first information content of a first information type, to display at least a second information content of a second information type and to display at least a third information content, wherein the third information content is of the first information type or of the second information type, wherein the first information type comprises generic information about the medicament and wherein the second information type comprises information about a momentary status, about an actual use or about a prior use of the drug delivery device, and a processor connected to the electronic display and configured to modify or to control a visual appearance of the electronic display by displaying at least a portion of the first information content and at least a portion of the third information content separately, simultaneously, sequentially or alternately on the electronic display, the method comprising:

displaying at least a portion of the first information content of the first information type on the electronic display; and separately, simultaneously, sequentially or alternately displaying at least a portion of the third information content on the electronic display, wherein the third information content is of the first information type or of the second information type, modifying at least a portion of one of the first information content and the second information content on the electronic display when receiving a sensor signal from an ambient sensor, which is located on the flexible substrate and connected to the processor, wherein the ambient sensor is configured to determine at least one of an ambient brightness, a variation of ambient air pressure, or to detect an orientation of the electronic label with regard to a field of gravity.

17. The method of claim 16, further comprising:

transmitting, to a data storage, first information contents of the first information type and second information contents of the second information type, to store the first information contents and the second information contents.

* * * * *